US009200058B2

(12) United States Patent
Park et al.

(10) Patent No.: US 9,200,058 B2
(45) Date of Patent: Dec. 1, 2015

(54) DUAL ANTAGONIST FOR TNF-α AND IL-21 FOR PREVENTING AND TREATING AUTOIMMUNE DISEASES

(75) Inventors: Young Woo Park, Daejeon (KR); Ki Won Jo, Gyeonggi-do (KR); Srok Ho Yoo, Daejeon (KR); Jung Yu, Daejeon (KR); Sun-Ha Yoon, Daejeon (KR); Ji Hyun Park, Daejeon (KR); Eun Jung Song, Daejeon (KR); Jong-Ho Lee, Gyeonggi-do (KR); Min Ji Seo, Seoul (KR); Sun Jung Cho, Gyeonggi-do (KR); Mi La Cho, Seoul (KR); Ho Youn Kim, Seoul (KR); Mi Kyung Park, Gyeonggi-do (KR); Hye Jwa Oh, Seoul (KR); Jin Sil Park, Seoul (KR); Yun Ju Woo, Seoul (KR); Jae Kyeong Byun, Chungcheongbuk-do (KR); Jun Geol Ryu, Gangwon-do (KR)

(73) Assignees: Korea Research Institute of Bioscience and Biotechnology, Daejeon (KR); Industry-Academic Cooperation Foundation, the Catholic University of Korea, Seoul (KR)

( * ) Notice: Subject to any disclaimer, the term of this patent is extended or adjusted under 35 U.S.C. 154(b) by 41 days.

(21) Appl. No.: 13/635,874

(22) PCT Filed: Mar. 18, 2011

(86) PCT No.: PCT/KR2011/001902
§ 371 (c)(1),
(2), (4) Date: Sep. 18, 2012

(87) PCT Pub. No.: WO2011/115458
PCT Pub. Date: Sep. 22, 2011

(65) Prior Publication Data
US 2013/0022642 A1    Jan. 24, 2013

(30) Foreign Application Priority Data
Mar. 19, 2010   (KR) .................. 10-2010-0024700

(51) Int. Cl.
*C07K 14/715*   (2006.01)

(52) U.S. Cl.
CPC ......... *C07K 14/7151* (2013.01); *C07K 14/7155* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 6,022,953 A * | 2/2000 | Ralph et al. ................... 530/351 |
| 2002/0110853 A1 | 8/2002 | Wiley | |
| 2006/0039902 A1 * | 2/2006 | Young et al. ............... 424/133.1 |
| 2008/0175896 A1 | 7/2008 | Winkles et al. | |

FOREIGN PATENT DOCUMENTS

| WO | WO 2004/003156 | 1/2004 |
|---|---|---|
| WO | WO 2006/043972 | 4/2006 |
| WO | WO 2007/009233 | 1/2007 |
| WO | WO 2010/003108 | 1/2010 |
| WO | WO 2010/003118 | 1/2010 |

OTHER PUBLICATIONS

Feldmann et al. Anti-TNF alpha therapy is useful in rheumatoid arthritis and Crohn's disease: analysis of the mechanism of action predicts utility in other diseases. Transplant Proc. Dec. 1998;30(8):4126-7.*

* cited by examiner

*Primary Examiner* — David Romeo
(74) *Attorney, Agent, or Firm* — Lathrop & Gage LLP

(57) ABSTRACT

The present invention relates to TNFR2-IL21R fusion protein acting as a double-antagonist to TNF-alpha (α) and IL-21. The composition containing the double antagonist to TNF-α and Il-21 (TNFR2-IL21R fusion protein), known as major causes of autoimmune rheumatoid arthritis, one of autoimmune diseases, can reduce the secretion of inflammatory cytokine, increase the secretion of anti-inflammatory cytokine, and suppress the differentiation of osteoclasts better than single proteins such as TNFR2-Fc and IL21R-Fc. The TNFR2-IL21R fusion protein of the present invention has not only excellent treatment effect on arthritis in CIA mouse model not also excellent treatment effect on autoimmune rheumatoid arthritis by increasing the expression of Treg, the immune suppressive cells. Therefore, the TNFR2-IL21R fusion protein of the present invention can be effectively used as an active ingredient for the composition for the prevention and treatment of autoimmune disease.

4 Claims, 12 Drawing Sheets

TNFR2   Total /culture Volume : 1mg/ml

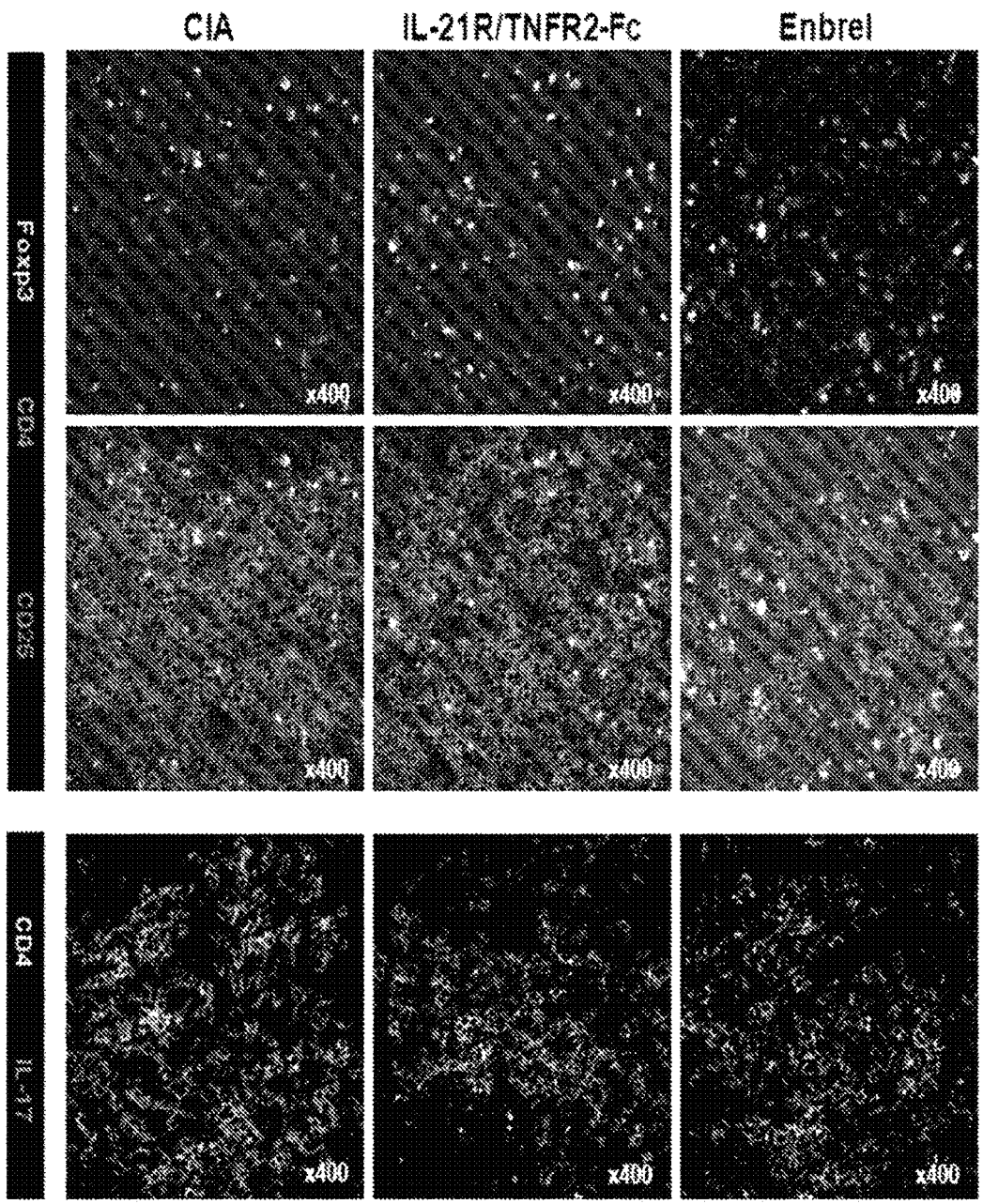

DUAL ANTAGONIST FOR TNF-α AND IL-21 FOR PREVENTING AND TREATING AUTOIMMUNE DISEASES

CROSS-REFERENCES TO RELATED APPLICATION

This patent application is a U.S. national phase under 35 U.S.C 371 of PCT/KR2011/001902 filed on Mar. 18, 2011, which claims the benefit of priority from Korean Patent Application No. 10-2010-0024700, filed on Mar. 19, 2010, the contents of which are incorporated herein by reference in its entirety.

REFERENCE TO SEQUENCE LISTING

A sequence listing containing SEQ ID NOS: 1-16 is submitted herewith and is specifically incorporated by reference.

BACKGROUND OF THE INVENTION

1. Field of the Invention

The present invention relates to a composition for the prevention and treatment of autoimmune diseases comprising a double antagonist to TNF-α and IL-21.

2. Description of the Related Art

Immune system plays a role in protecting human body from antigens, the harmful foreign materials. Such antigens are exemplified by bacteria, viruses, toxic materials, cancer cells, and blood or tissues of other people or animals. Immune system produces antibodies to destroy such harmful foreign materials introduced. However, if immune system is malfunctioning, the system cannot distinguish normal health organs of its own from harmful foreign antigens, and thus it destroys normal tissues as well. This reaction is called autoimmune disease. Such reaction shows allergic hypersensitivity reaction. Allergy is the reaction against foreign materials that are not harmful for human body, but in the case of autoimmune disease, reaction target includes normal tissues. The reason why immune system cannot distinguish normal organs from antigens is not known. There is only assumed theory that microorganisms such as bacteria or drugs might cause such disease in those who are inherited specifically with such genes that are vulnerable to autoimmune disease.

Autoimmune disease is exemplified by Hashimoto's thyroiditis, pernicious anemia, Addison's disease, type 1 diabetes, Rheumatoid arthritis, Systemic lupus erythematosus, dermatomyositis, Sjogren syndrome, Lupus erythematosus, Multiple sclerosis, Myasthenia gravis, Reactive arthritis, Grave's disease, and Celiac disease—sprue, etc.

The purpose of the treatment of autoimmune disease is to regulate autoimmune response and to recover damaged immune function. The treatment method can be varied from the type of autoimmune disease. For example, if there is a problem in blood, blood transfusion is required. If any abnormality is observed in bone, joint, or muscle, physical exercise or other functional treatment is required. In addition, drug is prescribed in order to regulate immune response. Such drug is called immunosuppressive medicine, which is exemplified by corticosteroids such as prednisone and nonsteroids such as cyclophosphamide, azathioprine, and tacrolimus, etc.

Even though 21 million people world-widely, which are approximately 1% of the total population on earth, catch rheumatoid arthritis (RA), one of autoimmune disease, the reason of this disease has not been disclosed, yet. The symptom of rheumatoid arthritis is symmetric systemic chronic inflammation in diarthrodial joint. When it gets worse, even joint dysfunction occurs. Make matter worse, such mal-functioning of autoimmune system brings inflammation and pain not only in joint but also in other tissues around joint and further in other organs of entire body including lung, skin, and eye with causing pain and osteoporosis, resulting in severe decrease of life-quality making normal daily life impossible.

The previous treatment of rheumatoid arthritis focused on delaying the development of the disease or alleviating the accompanied pain by the improvement of life habit, surgical operation, and administration of a therapeutic agent, with inhibiting infection but without expecting any improvement of joint functions. However, the recent treatment is aiming at the full recovery of joint function. This has been made possible by the development of anti-TNF antagonists, which has been regarded most dramatic discovery for the treatment of rheumatoid arthritis.

Tumor necrosis factor (TNF) is the pleiotropic cytokine, which plays an important role not only in inflammatory reaction but also in immune system. It is found in the joint of rheumatoid arthritis patient and colon of Crohn's disease patient. It has also been reported that tumor necrosis factor plays an important role in osteoclast, too. Therefore, all the treatment agents have been developed in order to inhibit TNF activity, precisely to interrupt signal transduction by binding to ligand belonging to TNF superfamily or to interrupt the bond between TNF ligand and receptor. To inhibit TNF signal transduction, monoclonal antibody against TNF ligand or recombinant protein has been used. Precisely, the treatment method using monoclonal antibody such as infliximab (Remicade) or adalimumab (Humira) has been used. And the treatment method using recombinant protein such as CTLA-4 Ig or entracept (Enbrel) has been also used. Infliximab, entracept, and adalimumab are the biological agents first accredited as rheumatoid arthritis treatment agents, which have been used for the past 10 years showing high efficiency. In addition to TNF, other cytokines have been targeted to develop a treatment agent. As DMARD (disease-modifying anti-rheumatic drugs) inhibiting interleukin, treatment agents have been developed targeting IL-6 or IL-1. However, the treatment effect is not as good as those of the anti-TNF agents.

Despite the excellent treatment effect, the anti-TNF agents have many problems to overcome. One example is the side effect of the administration of anti-TNF agents, which is TNF mechanism is stopped working, leading to mal-functioning of immune system with increasing risk of fungal or viral infection. Particularly, the chance of recurrence of dormant tuberculosis increases. In addition, demyelinating disorder such as multiple sclerosis or hematologic malignancies might be caused. According to rheumatoid society, chances of skin cancer development are higher in rheumatoid arthritis patients administered with anti-TNF agents than in those treated with the conventional therapeutic agents.

The treatment effect of the agent is not all the same among rheumatoid arthritis patients. Two thirds of the patients showed treatment effect, but one third of the patients were not improved. This result indicates that the treatment is limited by the medical history or genetic factors. Not only the pain from the disease but also the side effects accompanied by the treatment and the safety problems have to be considered and overcome. In the case of pregnant women having rheumatoid arthritis, the safety of fetus has been an issue when anti-TNF agent is administered. Scientists are faced with the task of developing diagnostic method to predict the treatment effect and the side effects thereby.

Interleukin (IL) is a kind of cytokine, which acts as a chemical signal between red blood cells. IL-2 was approved by FDA in 1992 for the treatment of liver cancer in late stage.

At that time, it was the first single immunotherapeutic agent. Since then, IL-2 has been used in the treatment of metastatic melanoma, too. IL-2 itself was used for the treatment of cancer or co-treated with vaccine. IL-2 helps immune system working to grow or differentiate cells fast. However, side effects have also been reported such as chills, fever, and fatigue, similar to those accompanied by cold, and confusion. IL-15 and IL-21, belonging to IL-2 family, have been studied as single cancer treatment agents or as adjuvants.

IL-21 is a kind of cytokine having α-helix structure. This cytokine induces inflammatory reaction in the middle of signal transduction using IL-21 receptor and γ-chain. IL-21 has been known to induce the maturation of NK cell precursors in bone marrow (Parrish-Novak J., et al., Nature, 408: 57-63, 2000). Particularly, IL-21 is reported to increase effector functions such as cytokine productivity and apoptotic activity of NK cells (Strengell M, et al., J Immunol., 170: 5464-5469, 2003; Brady J, et al., J Immunol., 172: 2048-2058, 2004). It also increases the effect of CD8+ T cells to accelerate anticancer response in endogenous adaptive immune system (Takaki R., et al., J Immunol., 175: 2167-2173, 2005; Moroz A., et al., Immunol, 173: 900-909, 2004). IL-21 is also reported to activate NK cells separated from human peripheral blood (Parrish-Novak J., et al., Nature, 408: 57-63, 2000) and play an important role in inducing mature NK cells from hematopoietic stem cells separated from cord blood (Sonia A. P, et al., Int. immunol., 18: 49-58, 2006).

The present inventors tried to develop a novel therapeutic agent for autoimmune disease which is advantageous in overcoming the limitation of efficiency and safety matter of the conventional single antagonist used as an anti-TNF treatment agent. Precisely, the inventors constructed TNFR2-IL21R fusion protein having antagonism against TNF-alpha (α) and IL-21. Then, the inventors confirmed with the fusion protein that the expressions of inflammatory cytokines such as IL-21 and IL-17 and RORc were all reduced but the expression of FoxP3 and the secretion of anti-inflammatory cytokine IL-10 were increased. The inventors further confirmed that TNFR2-IL21R fusion protein inhibited the differentiation of osteoclasts and reduced the expression of cathespin K, which was greater than when TNFR2-Fc or IL21R-Fc was treated. In CIA (collagen induced arthritis) mouse model, the present inventors confirmed that the TNFR2-IL21R fusion protein of the invention had not only arthritis treatment effect but also autoimmune arthritis treatment effect by increasing the expression of immune inhibitor Treg cells. The present inventors finally completed this invention by confirming the great possibility of the TNFR2-IL21R fusion protein of the invention as a treatment agent for autoimmune rheumatoid arthritis.

SUMMARY OF THE INVENTION

It is an object of the present invention to provide a composition for the prevention and treatment of autoimmune disease comprising TNFR2-IL21R fusion protein acting as a double antagonist to TNF-α and IL-21 as an active ingredient.

To achieve the above object, the present invention provides a fusion protein in which the fragment containing TNFR2 (tumor necrosis factor receptor type 2) protein or extracellular domain of the said TNFR2 is linked to the fragment containing IL21R (interleukin-21 receptor) protein or extracellular domain of the said IL21R.

The present invention also provides a polynucleotide encoding the TNFR2-IL21R fusion protein.

The present invention further provides an expression vector containing the polynucleotide encoding the TNFR2-IL21 fusion protein.

The present invention also provides a transformant obtained by transfecting host cells with the expression vector comprising the polynucleotide encoding the TNFR2-IL21R fusion protein.

The present invention also provides a composition for the prevention and treatment of autoimmune disease comprising the TNFR2-IL21R fusion protein as an active ingredient.

The present invention also provides a method for the treatment of autoimmune disease containing the step of administering pharmaceutically effective dose of the TNFR2-IL21R fusion protein to a subject having autoimmune disease.

The present invention also provides a method for the prevention of autoimmune disease containing the step of administering pharmaceutically effective dose of the TNFR2-IL21R fusion protein to a subject.

In addition, the present invention provides a fusion protein of the present invention for the prevention and treatment of autoimmune disease.

Advantageous Effect

As explained hereinbefore, the present invention relates to a composition comprising TNFR2-IL21R fusion protein characterized by antagonism against TNF-α and IL-21, which have presumed to be major causes for autoimmune rheumatoid arthritis, one of autoimmune diseases. The TNFR2-IL-21R fusion protein inhibited the secretion of inflammatory cytokine, increased the production of anti-inflammatory cytokine, and had excellent inhibitory effect on osteoclast differentiation. Besides, the fusion protein showed excellent alleviating effect on infiltration, inflammation, and cartilage destruction in joint in CIA mouse model. The fusion protein of the invention was also proved to increase the expression of Treg cells, the immune suppressive cells, to bring the treatment effect on autoimmune rheumatoid arthritis. Therefore, the TNFR2-IL21R fusion protein of the present invention can be effectively used as an active ingredient for the composition having the preventive and therapeutic effect on autoimmune diseases.

BRIEF DESCRIPTION OF THE DRAWINGS

The application of the preferred embodiments of the present invention is best understood with reference to the accompanying drawings, wherein:

FIG. 12A is a graph illustrating the Clinical Score observed after the administration of the TNFR2-IL21R fusion protein of the present invention or Enbrel to CIA mouse model;

↑: the time of administration of TNFR2-IL21R fusion protein or Enbrel;

Arthritis: negative control—CIA (collagen induced arthritis) animal model group treated with nothing;

IL21R/TNFR2-Fc: CIA animal model group treated with TNFR2-IL21R fusion protein; and Enbrel: CIA animal model group treated with the arthritis treatment agent Enbrel;

FIG. 12B is a graph illustrating the Incidence observed after the administration of the TNFR2-IL21R fusion protein of the present invention or Enbrel to CIA mouse model;

↑: the time of administration of TNFR2-IL21R fusion protein or Enbrel;

Arthritis: negative control—CIA (collagen induced arthritis) animal model group treated with nothing;

IL21R/TNFR2-Fc: CIA animal model group treated with TNFR2-IL21R fusion protein; and Enbrel: CIA animal model group treated with the arthritis treatment agent Enbrel.

Figure 13:
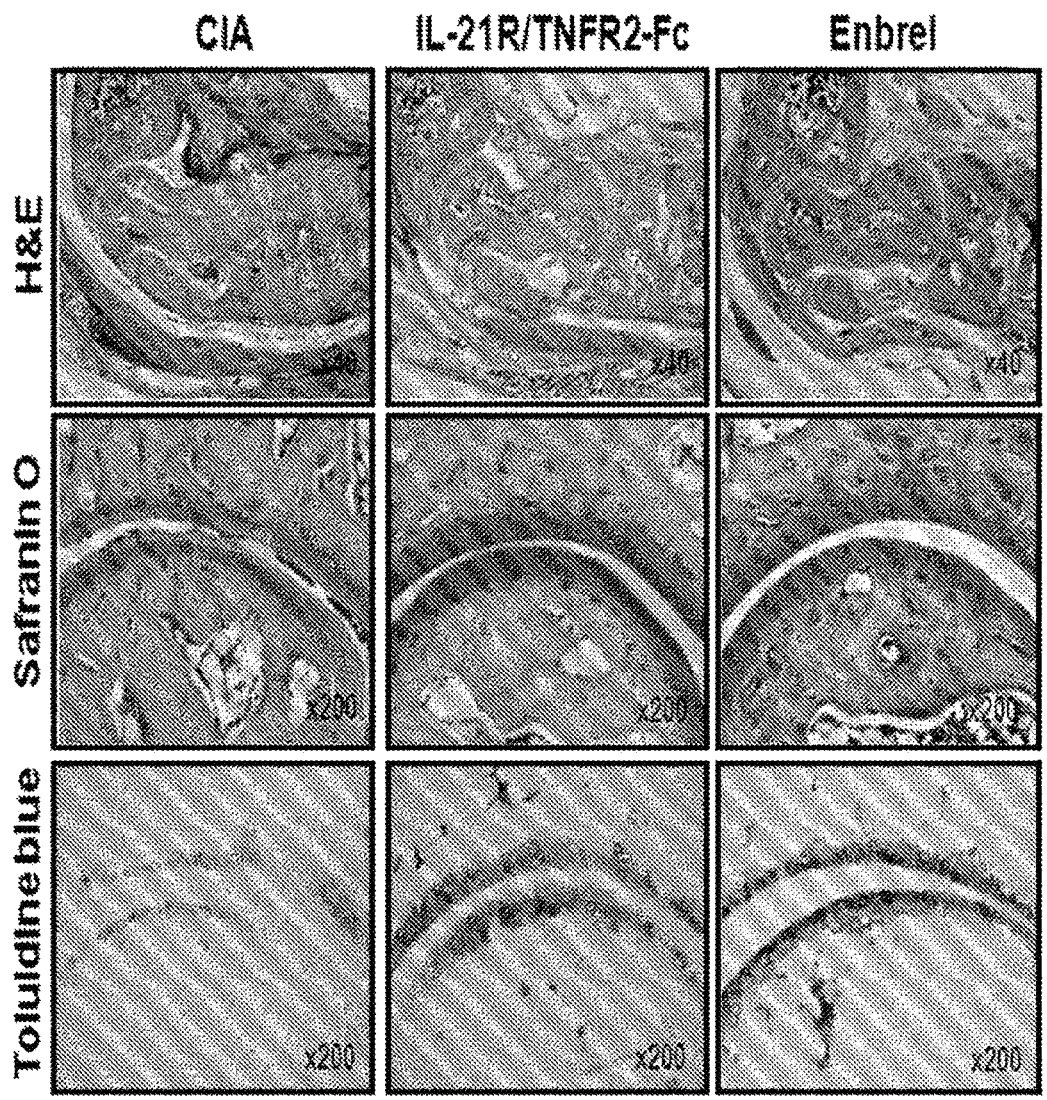

FIG. 13 is a set of photographs illustrating the arthritis alleviating effect of TNFR2-IL21R fusion protein in CIA mouse model, confirmed by immunohistostaining method:

CIA: negative control—CIA (collagen induced arthritis) animal model group treated with nothing;

IL21R/TNFR2-Fc: CIA animal model group treated with TNFR2-IL21R fusion protein; and Enbrel: CIA animal model group treated with the arthritis treatment agent Enbrel.

Figure 14:
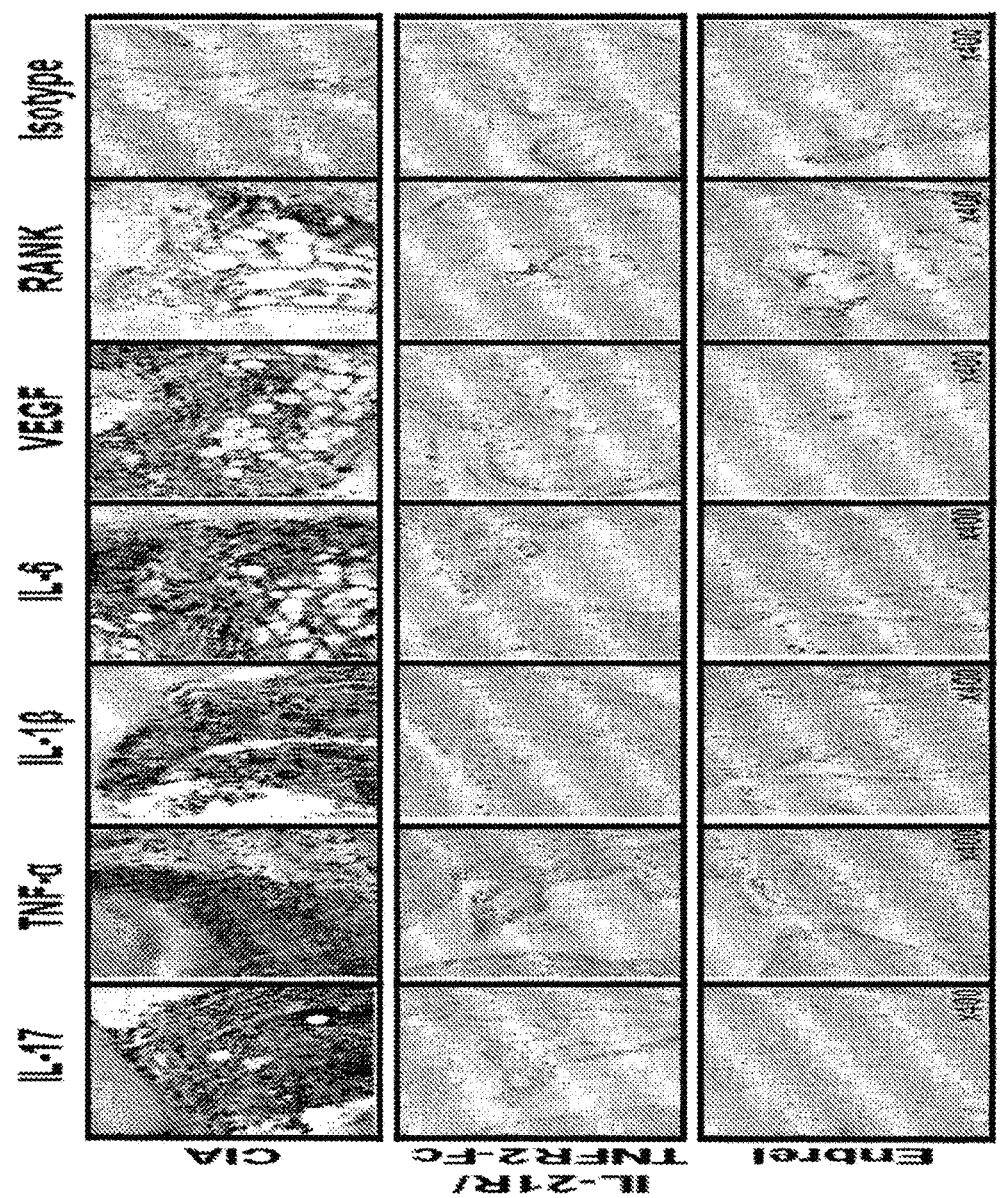

FIG. 14 is a set of photographs illustrating the anti-inflammatory effect of TNFR2-IL21R fusion protein in CIA mouse model, confirmed by immunohistostaining method:

CIA: negative control—CIA (collagen induced arthritis) animal model group treated with nothing;

IL21R/TNFR2-Fc: CIA animal model group treated with TNFR2-IL21R fusion protein; and Enbrel: CIA animal model group treated with the arthritis treatment agent Enbrel.

Figure 15:
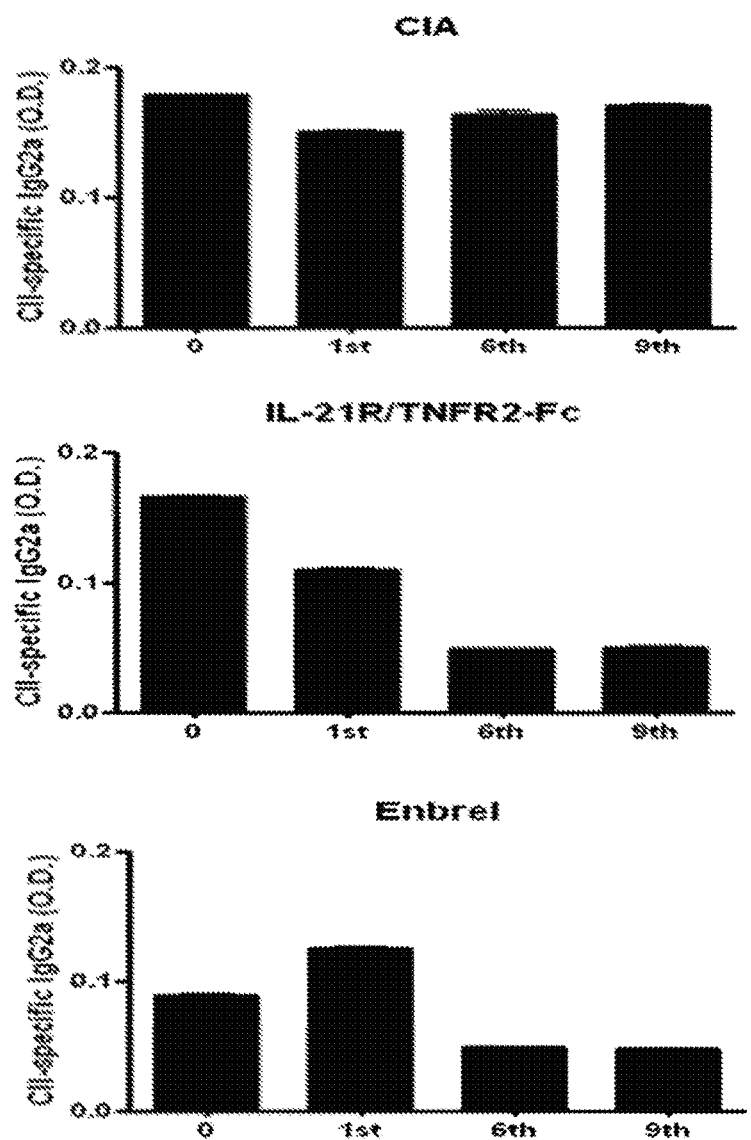

FIG. 15 is a set of graphs illustrating the CII specific IgG2a production in CIA mouse model:

0: before the administration of TNFR2-IL21R fusion protein or Enbrel;

1st: first administration of TNFR2-IL21R fusion protein or Enbrel;

6th: sixth administration of TNFR2-IL21R fusion protein or Enbrel;

9th: ninth administration of TNFR2-IL21R fusion protein or Enbrel;

CIA: negative control—CIA (collagen induced arthritis) animal model group treated with nothing;

IL21R/TNFR2-Fc: CIA animal model group treated with TNFR2-IL21R fusion protein; and Enbrel: CIA animal model group treated with the arthritis treatment agent Enbrel.

FIG. 16 is a set of photographs illustrating the expressions of Th17 and Treg cells in the spleen of CIA mouse model, confirmed by immunohistostaining method:

CIA: negative control—CIA (collagen induced arthritis) animal model group treated with nothing;

IL21R/TNFR2-Fc: CIA animal model group treated with TNFR2-IL21R fusion protein; and Enbrel: CIA animal model group treated with the arthritis treatment agent Enbrel.

DESCRIPTION OF THE PREFERRED EMBODIMENTS

Hereinafter, the present invention is described in detail.

The present invention provides a fusion protein in which the fragment containing TNFR2 (tumor necrosis factor receptor type 2) protein or extracellular domain of the said TNFR2 is linked to the fragment containing IL21R (interleukin-21 receptor) protein or extracellular domain of the said IL21R.

In the TNFR2-IL21R fusion protein, the fragment containing extracellular domain of TNFR2 is preferably the polypeptide containing the sequence ranging from the $23^{rd}$~$179^{th}$ residue of the amino acid sequence represented by SEQ. ID. NO: 2, but not always limited thereto. In the TNFR2-IL21R fusion protein, the fragment containing extracellular domain of IL21R is preferably the polypeptide containing the sequence ranging from the $21^{st}$~$231^{st}$ residue of the amino acid sequence represented by SEQ. ID. NO: 2, but not always limited thereto. The fusion protein preferably has the amino acid sequence represented by SEQ. ID. NO: 1, but not always limited thereto. It is also preferred that the TNFR2-IL21R fusion protein is composed of 200~250 amino acids, but not always limited thereto.

The TNFR2-IL21R fusion protein preferably contains the fragment originated from constant domain of antibody heavy chain, but not always limited thereto. Fc domain included in the TNFR2-IL21R fusion protein is preferably selected from the group consisting of IgA, IgD, IgE, IgG, and IgM, and more preferably it contains the whole or a part of CH2 and CH3 constant domain, but not always limited thereto.

In the TNFR2-IL21R fusion protein, carboxyl-terminal and amino-terminal of extracellular soluble domains of TNFR2 and IL21R preferably contain the whole or a part of constant domain of antibody heavy chain, but not always limited thereto. The TNFR2-IL21R fusion protein preferably contains the constant domain of antibody heavy chain of at least 2 equivalents, but not always limited thereto. Two Fc heavy chains therein are preferably conjugated by disulfide bond or another covalent bond, but not always limited thereto. TNFR2 and IL21R parts of the TNFR2-IL21R fusion protein preferably contain extracellular soluble domain of TNFR2 and IL21R of at least 2 equivalents, but not always limited thereto.

The TNFR2-IL21R fusion protein of the present invention is preferably prepared by the method comprising the following steps, but not always limited thereto:

1) performing PCR (polymerase chain reaction) with IL21R primer using DNA library as a template;
2) performing PCR with TNFR2 primer using DNA library as a template;
3) performing PCR with a primer encoding TNFR2-IL21R fusion gene using the PCR products of step 1) and step 2) as templates;
4) digesting the PCR product of step 3) with a restriction enzyme;
5) digesting the expression vector pYK-602-HIS-Fc with a restriction enzyme;
6) performing ligation of the plasmids digested with the restriction enzymes of step 4) and step 5);
7) transforming the TNFR2-IL21R fusion protein completed with the ligation reaction of step 6);
8) inoculating the protein on LB plate after completion of the transformation of step 7);
9) performing PCR using the colony generated in step 8);
10) transfecting 293E cells with the TNFR2-IL21R fusion protein confirmed in step 9);
11) purifying the TNFR2-IL21R fusion protein expressed in the 293E cells of step 10) from the cell culture medium;
12) eliminating cytotoxicity from the TNFR2-IL21R fusion protein purified in step 11); and
13) confirming binding affinity of the TNFR2-IL21R fusion protein purified in step 12).

In the preparation method of the present invention, the construction of the vector is preferably performed by PCR using DNA library, and the said DNA library is preferably constructed from liver, placenta, pancreas, and liver tissues, but not always limited thereto.

The present invention also provides a polynucleotide encoding the TNFR2-IL21R fusion protein.

The present invention further provides an expression vector containing the polynucleotide encoding the TNFR2-IL21 fusion protein.

The expression vector herein is preferably pYK602-HIS-Fc, but not always limited thereto.

The present invention also provides a transformant obtained by transfecting host cells with the expression vector comprising the polynucleotide encoding the TNFR2-IL21R fusion protein.

The transformant herein is preferably $E.\ coli$ DH5α, but not always limited thereto.

Figure 1:
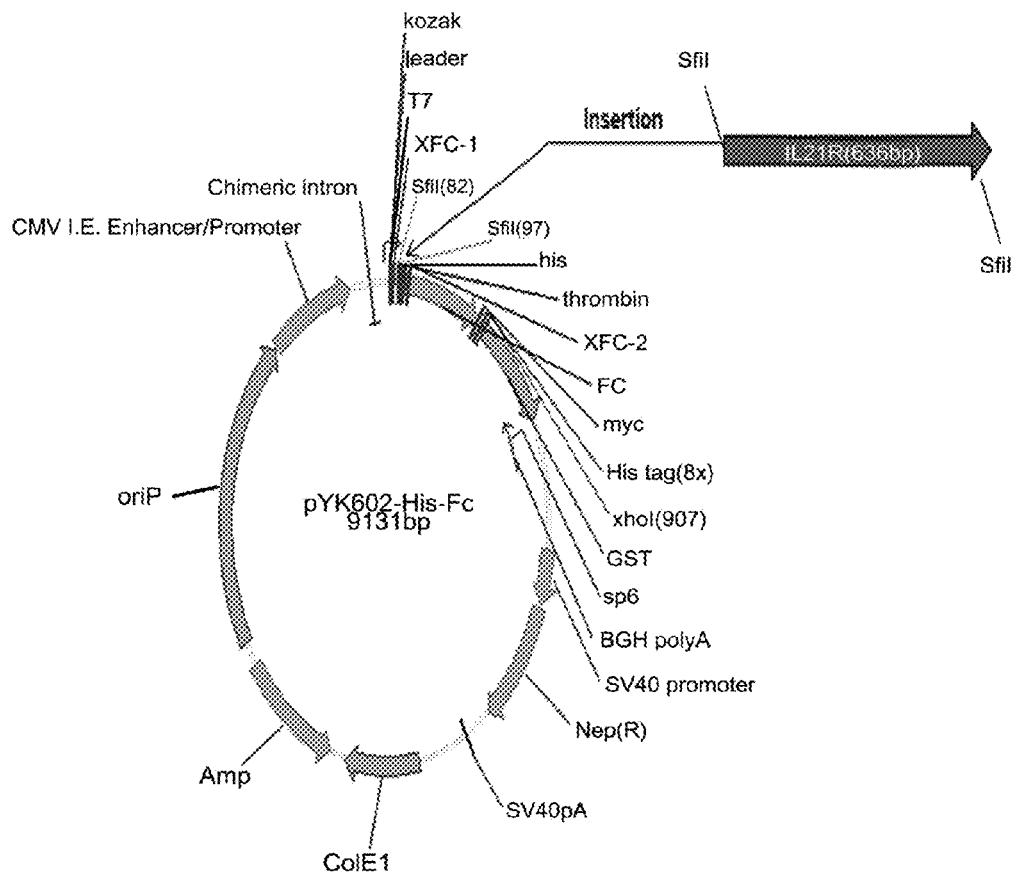
FIG. 1 is a diagram illustrating the structure of IL21R-Fc in which IL21R gene has been cloned in the expression vector pYK602-HIS-Fc.

In a preferred embodiment of the present invention, IL21R and TNFR2 genes were amplified by PCR to subclone IL21R and TNFR2 into the expression vector pYK602-HIS-Fc. Each of the amplified PCR products was ligated in the expression vector pYK602-HIS-Fc to construct TNFR2-Fc and IL21R-Fc (see FIG. 1 and FIG. 3). The constructed TNFR2-Fc and IL21R-Fc were transfected in 293E cells. Upon completion of the transfection, the produced and purified protein (single antagonist to IL-21) was confirmed by western blot (see FIG. 2 and FIG. 4).

Figure 5:
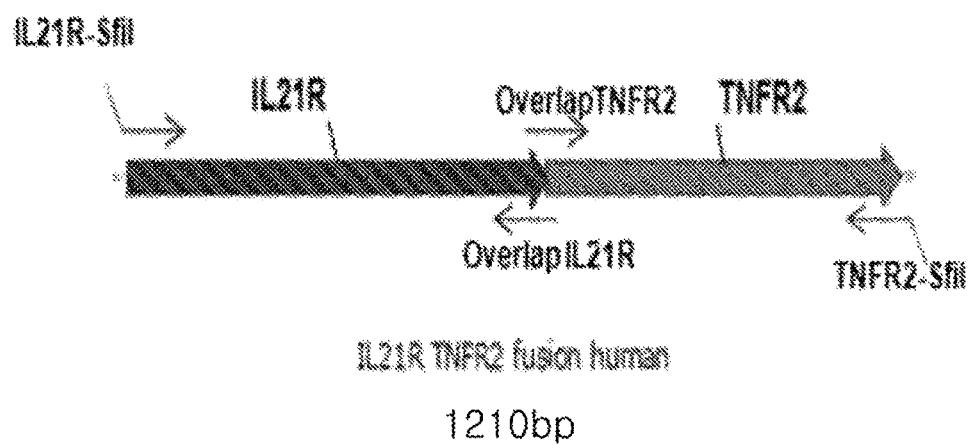
FIG. 5 is a diagram illustrating the structure of PCR primer used for the construction of the expression vector inducing the expression of TNFR2-IL21R fusion protein.
Figure 6:
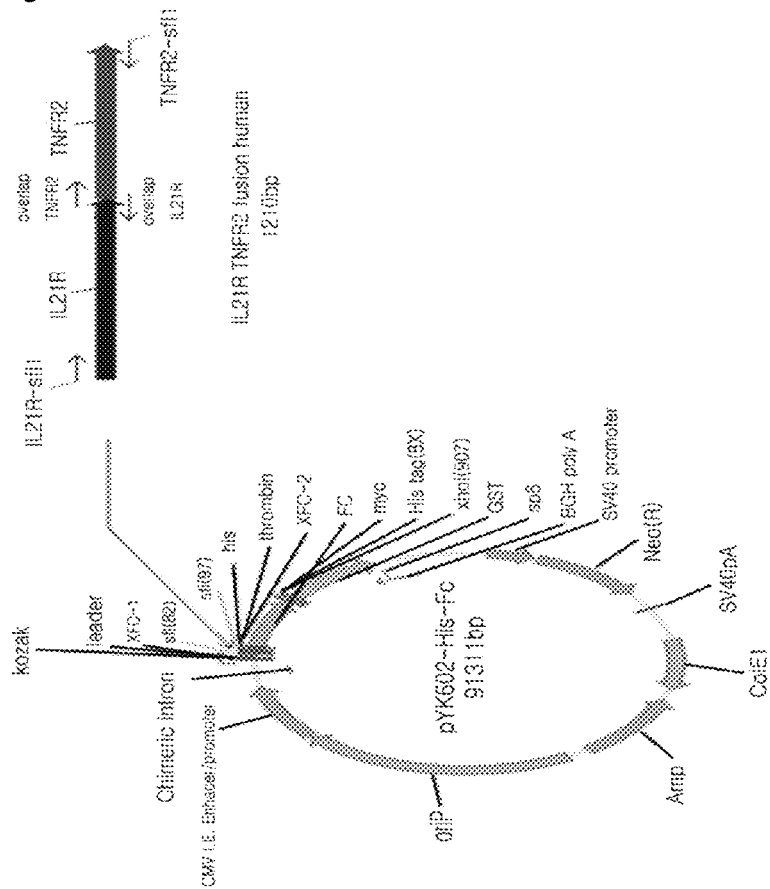
FIG. 6 is a set of diagrams illustrating the structure of TNFR2-IL21R fusion protein prepared by cloning TNFR2 gene together with IL21R gene in the expression vector pYK602-HIS-Fc.

IL21R and TNFR2 genes were amplified by PCR using DNA library mixture (mixture of kidney, placenta, pancreas, and liver) as a template. After constructing a primer to amplify IL21R and TNFR2 fusion gene (see FIG. 5), PCR was performed with the gene encoding TNFR2-IL21R fusion protein (double antagonist to TNF-α and IL-21) by using the amplified product above as a template. The amplified PCR product proceeded to ligation into the expression vector pYK602-HIS-Fc, leading to the construction of TNFR2-IL21R fusion protein expression vector (see FIG. 6 and FIG. 7).

Figure 8:
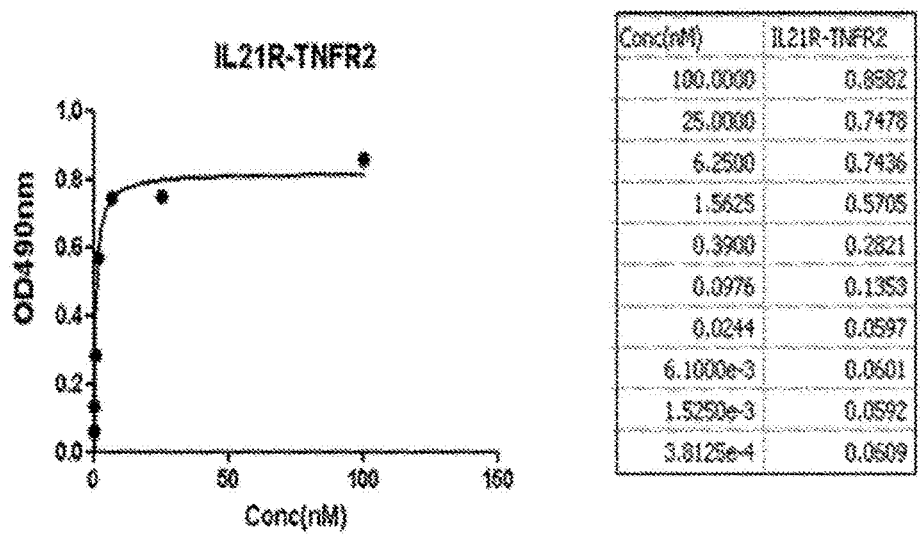
FIG. 8 is a graph illustrating the binding affinity between TNFR2-IL21R fusion protein and its ligand TNF-α and IL-21.

In addition, binding affinity between TNFR2-IL21R fusion protein and one of its ligands TNF-α was investigated and as a result, it was confirmed that the TNFR2-IL21R fusion protein had high binding affinity to TNF-α and IL-21 (see FIG. 8).

The present invention also provides a composition for the prevention and treatment of autoimmune disease comprising the TNFR2-IL21R fusion protein as an active ingredient.

In the TNFR2-IL21R fusion protein, the fragment containing extracellular domain of TNFR2 is preferably the polypeptide containing the sequence ranging from the $23^{rd}$~$179^{th}$ residue of the amino acid sequence represented by SEQ. ID. NO: 2, but not always limited thereto. In the TNFR2-IL21R fusion protein, the fragment containing extracellular domain of IL21R is preferably the polypeptide containing the sequence ranging from the $21^{st}$~$231^{st}$ residue of the amino acid sequence represented by SEQ. ID. NO: 3, but not always limited thereto. The fusion protein preferably has the amino acid sequence represented by SEQ. ID. NO: 1, but not always limited thereto. It is also preferred that the TNFR2-IL21R fusion protein is composed of 200~250 amino acids, but not always limited thereto.

The TNFR2-IL21R fusion protein preferably contains the fragment originated from constant domain of heavy chain of antibody, but not always limited thereto. Fc domain included in the TNFR2-IL21R fusion protein is preferably selected from the group consisting of IgA, IgD, IgE, IgG, and IgM, and more preferably it contains the whole or a part of CH2 and CH3 constant domain, but not always limited thereto.

In the TNFR2-IL21R fusion protein, carboxyl-terminal and amino-terminal of extracellular soluble domains of TNFR2 and IL21R preferably contain the whole or a part of constant domain of antibody heavy chain, but not always limited thereto. The TNFR2-IL21R fusion protein preferably contains the constant domain of antibody heavy chain of at least 2 equivalents, but not always limited thereto. Two Fc heavy chains therein are preferably conjugated by disulfide bond or another covalent bond, but not always limited thereto. TNFR2 and IL21R parts of the TNFR2-IL21R fusion protein preferably contain extracellular soluble domain of TNFR2 and IL21R of at least 2 equivalents, but not always limited thereto.

The said autoimmune disease is preferably the one selected from the group consisting of autoimmune rheumatoid arthritis, lupus, myasthenia gravis, ankylosing spondylitis, hyperthyroidism, hypothyroidism, ulcerative colitis, Crohn's disease, valvular heart disease, multiple sclerosis, Scleroderma, and autoimmune hepatitis, and more preferably autoimmune rheumatoid arthritis, but not always limited thereto.

In a preferred embodiment of the present invention, Th17 cells were treated with TNFR2-Fc, IL21R-Fc, and TNFR2-IL21R fusion protein, constructed above. As a result, when TNFR2-IL21R fusion protein was treated, the inflammatory cytokines IL-21 and IL17, and the transcription factor RORc were all down-regulated significantly, compared with when TNFR2-Fc or IL21R-Fc was treated (see FIG. 9). When TNFR2-IL21R fusion protein was treated, the inflammatory cytokine secreted in Th17 was significantly decreased, compared with when TNFR2-Fc or IL21R-Fc was treated (see FIG. 9). TNFR2-Fc, IL21R-Fc, and TNFR2-IL21R fusion protein were treated respectively to the Th17-polarizing condition and then the anti-inflammatory cytokine IL-10 level was measured by ELISA. As a result, the expression of FoxP3 and the secretion of IL-10 were significantly increased when the cells were treated with TNFR2-IL21R fusion protein, compared with when the cells were treated with TNFR2-Fc or IL21R-Fc (see FIG. 10). In addition, after treating TNFR2-Fc, IL21R-Fc, and TNFR2-IL21R fusion protein respectively, the differentiation of osteoclasts was inhibited, that was confirmed by TRAP staining and by observing the increase of Cathespin K expression (see FIG. 11).

In a preferred embodiment of the present invention, CIA (collagen induced arthritis) mouse model was constructed to confirm the in vivo treatment effect of the TNFR2-IL21R fusion protein of the present invention on arthritis. Then, the mouse model was treated with the TNFR2-IL21R fusion protein of the present invention. As a result, the treatment effect on arthritis was confirmed (see FIG. 12). Precisely, infiltration and inflammation in joint was reduced and so was cartilage destruction (see FIG. 13). The expressions of inflammatory factors were also reduced (see FIG. 14), and the generation of CII specific IgG2a, administered to construct the arthritis induced mouse model, was inhibited (see FIG. 15). The arthritis treatment effect or alleviation effect of the fusion protein of the present invention was similar to or better than that of Enbrel, being used as of today as an arthritis treatment agent. Spleen tissue involved in immune response was extracted from CIA mouse model treated with the TNFR2-IL21R fusion protein of the present invention, followed by observation of the expressions of Th17 and Treg cells. As a result, the expression of Th17 cells (CD4+IL-17+) expressing inflammatory factors was decreased, while the expression of Treg cells (CD4+CD25+Foxp3+), the immune suppressive cells from autoimmune response, was increased (see FIG. 16).

In conclusion, the TNFR2-IL21R fusion protein reduces the inflammatory cytokine IL-17 production, which is more significant than TNFR2-Fc and IL21R-Fc do, increases the anti-inflammatory cytokine IL-10 generation better than TNFR2-Fc and IL21R-Fc do, and demonstrates autoimmune rheumatoid arthritis alleviation or treatment effect in CIA mouse model. Therefore, the TNFR2-IL21R fusion protein of the present invention can be effectively used as an active ingredient for the composition for the prevention and treatment of autoimmune disease.

The pharmaceutically effective dosage of the TNFR2-IL21R fusion protein of the present invention can be determined by considering various factors such as administration method, target area, patient condition, etc. Thus, the dosage for human body has to be determined with the consideration of safety and efficiency at the same time. It is also possible to predict the effective dosage based on the effective dosage confirmed by animal test. Various factors that have to be considered for the determination of the effective dosage are described in the following articles: Hardman and Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), Mack Publishing Co.

The pharmaceutical composition of the present invention can include any generally used carrier, diluent, excipient, or a combination of at least two of those. The pharmaceutically acceptable carrier can be any carrier that is able to deliver the TNFR2-IL21R fusion protein of the present invention in human body without limitation, which is exemplified by the compounds described in Merck Index, 13$^{th}$ ed., Merck & Co. Inc., such as saline, sterilized water, Ringer's solution, buffered saline, dextrose solution, maltodextrin solution, glycerol, ethanol, liposome and a mixture comprising one or more of those components. If necessary, a general additive such as antioxidant, buffer, and bacteriostatic agent can be additionally added. The composition of the present invention can be formulated in different forms including aqueous solutions, suspensions and emulsions for injection, pills, capsules, granules or tablets by mixing with diluents, dispersing agents, surfactants, binders and lubricants. The composition can further be prepared in suitable forms according to ingredients by following the method represented in Remington's Pharmaceutical Science Mack Publishing Company, Easton Pa., 18th, 1990).

The composition of the present invention can additionally include one or more effective ingredients having the same or similar function to the active ingredient. The composition of the present invention can include the said protein by 0.0001-10 weight %, and preferably by 0.001-1 weight % by the total weight of the composition.

The pharmaceutical composition of the present invention can be administered orally or parenterally (for example, intravenous, hypodermic, peritoneal or local injection). The effective dosage of the composition can be determined according to weight, age, gender, health condition, diet, administration frequency, administration method, excretion and severity of a disease. The dosage is 0.001~100 mg/kg per day and preferably 0.01~10 mg/kg per day, and administration frequency is once a day or preferably a few times a day.

The present invention also provides a method for the treatment of autoimmune disease containing the step of administering pharmaceutically effective dose of the TNFR2-IL21R fusion protein to a subject having autoimmune disease.

The present invention also provides a method for the prevention of autoimmune disease containing the step of administering pharmaceutically effective dose of the TNFR2-IL21R fusion protein to a subject.

In the TNFR2-IL21R fusion protein, the fragment containing extracellular domain of TNFR2 is preferably the polypeptide containing the sequence ranging from the 23$^{rd}$~179$^{th}$ residue of the amino acid sequence represented by SEQ. ID. NO: 2, but not always limited thereto. In the TNFR2-IL21R fusion protein, the fragment containing extracellular domain of IL21R is preferably the polypeptide containing the sequence ranging from the 21$^{st}$~231$^{st}$ residue of the amino acid sequence represented by SEQ. ID. NO: 3, but not always limited thereto. The fusion protein preferably has the amino acid sequence represented by SEQ. ID. NO: 1, but not always limited thereto. It is also preferred that the TNFR2-IL21R fusion protein is composed of 200~250 amino acids, but not always limited thereto.

The TNFR2-IL21R fusion protein preferably contains the fragment originated from constant domain of heavy chain of antibody, but not always limited thereto. Fc domain included in the TNFR2-IL21R fusion protein is preferably selected from the group consisting of IgA, IgD, IgE, IgG, and IgM, and more preferably it contains the whole or a part of CH2 and CH3 constant domain, but not always limited thereto.

In the TNFR2-IL21R fusion protein, carboxyl-terminal and amino-terminal of extracellular soluble domains of TNFR2 and IL21R preferably contain the whole or a part of constant domain of antibody heavy chain, but not always limited thereto. The TNFR2-IL21R fusion protein preferably contains the constant domain of antibody heavy chain of at least 2 equivalents, but not always limited thereto. Two Fc heavy chains therein are preferably conjugated by disulfide bond or another covalent bond, but not always limited thereto. TNFR2 and IL21R parts of the TNFR2-IL21R fusion protein preferably contain extracellular soluble domain of TNFR2 and IL21R of at least 2 equivalents, but not always limited thereto.

The said autoimmune disease is preferably the one selected from the group consisting of autoimmune rheumatoid arthritis, lupus, myasthenia gravis, ankylosing spondylitis, hyperthyroidism, hypothyroidism, ulcerative colitis, Crohn's disease, valvular heart disease, multiple sclerosis, Scleroderma, and autoimmune hepatitis, and more preferably autoimmune rheumatoid arthritis, but not always limited thereto.

It was confirmed that the TNFR2-IL21R fusion protein of the present invention reduced the production of the inflammatory cytokine IL-17, which was more significant than TNFR2-Fc and IL21R-Fc did, but increased the production of the anti-inflammatory cytokine IL-10 better than TNFR2-Fc and IL21R-Fc did. In addition, the inhibitory effect on osteoclast differentiation of the fusion protein was more peculiar than that of TNFR2-Fc and IL21R-Fc, so that the fusion protein can be effectively used for the treatment of autoimmune disease.

The pharmaceutically effective dosage of the TNFR2-IL21R fusion protein of the present invention can be determined by considering various factors such as administration method, target area, patient condition, etc. Thus, the dosage for human body has to be determined with the consideration of safety and efficiency at the same time. It is also possible to predict the effective dosage based on the effective dosage confirmed by animal test. Various factors that have to be considered for the determination of the effective dosage are described in the following articles: Hardman and Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), Mack Publishing Co.

The pharmaceutical composition of the present invention can include any generally used carrier, diluent, excipient, or a combination of at least two of those. The pharmaceutically acceptable carrier can be any carrier that is able to deliver the TNFR2-IL21R fusion protein of the present invention in human body without limitation, which is exemplified by the compounds described in Merck Index, $13^{th}$ ed., Merck & Co. Inc., such as saline, sterilized water, Ringer's solution, buffered saline, dextrose solution, maltodextrin solution, glycerol, ethanol, liposome and a mixture comprising one or more of those components. If necessary, a general additive such as antioxidant, buffer, and bacteriostatic agent can be additionally added. The composition of the present invention can be formulated in different forms including aqueous solutions, suspensions and emulsions for injection, pills, capsules, granules or tablets by mixing with diluents, dispersing agents, surfactants, binders and lubricants. The composition can further be prepared in suitable forms according to ingredients by following the method represented in Remington's Pharmaceutical Science (Mack Publishing Company, Easton Pa., 18th, 1990).

The composition of the present invention can additionally include one or more effective ingredients having the same or similar function to the active ingredient. The composition of the present invention can include the said protein by 0.0001-10 weight %, and preferably by 0.001-1 weight % by the total weight of the composition.

The pharmaceutical composition of the present invention can be administered orally or parenterally (for example, intravenous, hypodermic, peritoneal or local injection). The effective dosage of the composition can be determined according to weight, age, gender, health condition, diet, administration frequency, administration method, excretion and severity of a disease. The dosage is 0.001~100 mg/kg per day and preferably 0.01~10 mg/kg per day, and administration frequency is once a day or preferably a few times a day.

In addition, the present invention provides a fusion protein for the prevention and treatment of autoimmune disease.

In the TNFR2-IL21R fusion protein, the fragment containing extracellular domain of TNFR2 is preferably the polypeptide containing the sequence ranging from the $23^{rd}\sim179^{th}$ residue of the amino acid sequence represented by SEQ. ID. NO: 2, but not always limited thereto. In the TNFR2-IL21R fusion protein, the fragment containing extracellular domain of IL21R is preferably the polypeptide containing the sequence ranging from the $21^{st}\sim231^{st}$ residue of the amino acid sequence represented by SEQ. ID. NO: 3, but not always limited thereto. The fusion protein preferably has the amino acid sequence represented by SEQ. ID. NO: 1, but not always limited thereto. It is also preferred that the TNFR2-IL21R fusion protein is composed of 200~250 amino acids, but not always limited thereto.

The TNFR2-IL21R fusion protein preferably contains the fragment originated from constant domain of heavy chain of antibody, but not always limited thereto. Fc domain included in the TNFR2-IL21R fusion protein is preferably selected from the group consisting of IgA, IgD, IgE, IgG, and IgM, and more preferably it contains the whole or a part of CH2 and CH3 constant domain, but not always limited thereto.

In the TNFR2-IL21R fusion protein, carboxyl-terminal and amino-terminal of extracellular soluble domains of TNFR2 and IL21R preferably contain the whole or a part of constant domain of antibody heavy chain, but not always limited thereto. The TNFR2-IL21R fusion protein preferably contains the constant domain of antibody heavy chain of at least 2 equivalents, but not always limited thereto. Two Fc heavy chains therein are preferably conjugated by disulfide bond or another covalent bond, but not always limited thereto. TNFR2 and IL21R parts of the TNFR2-IL21R fusion protein preferably contain extracellular soluble domain of TNFR2 and IL21R of at least 2 equivalents, but not always limited thereto.

The said autoimmune disease is preferably the one selected from the group consisting of autoimmune rheumatoid arthritis, lupus, myasthenia gravis, ankylosing spondylitis, hyperthyroidism, hypothyroidism, ulcerative colitis, Crohn's disease, valvular heart disease, multiple sclerosis, Scleroderma, and autoimmune hepatitis, and more preferably autoimmune rheumatoid arthritis, but not always limited thereto.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Construction of IL21R-Fc

<1-1> Construction of IL21R-Fc Expression Vector

To construct IL21R-Fc expression vector, IL21R gene was amplified by PCR using DNA library mixture (mixture of kidney, placenta, pancreas, and liver; purchased from 21C Frontier Human GENE Bank (Korea Research Institute of Bioscience and Biotechnology), Clone ID: hMU007690, plate No. IRAH-24-A10, vector: pOTB7.) as a template with a forward primer containing Sfi I site (SEQ. ID. NO: 4:

5'-aggggggccgtgggggcccccgacctcgtctgctacac-3') and a reverse primer (SEQ. ID. NO: δ: 5'-tagcggccgacgcggccaattcctt-taactcctctgact-3'). The PCR product was treated with Sfi I, and then subcloned into pYK602-HIS-Fc. PCR reaction mixture was prepared as follows. 100 ng of template DNA, 2.5 unit of pfu polymerase (Genotech, Korea), 10 pmole/50 μl of each primer, and distilled water were mixed to make the final volume 50 μl. PCR was performed as follows; predenaturation at 94° C. for 2 minutes, denaturation at 94° C. for 30 seconds, annealing at 58° C. for 30 seconds, polymerization at 72° C. for 1 minute, 30 cycles from denaturation to polymerization, and final extension at 72° C. for 10 minutes.

The amplified PCR product and the vector were digested with SfiI, followed by reaction at 37° C. for 4 hours. Purification was then performed by using gel purification kit (QIAGEN, #28706, USA). The ratio of the amplified PCR product to the vector was 3(150 μg):1(50 μg), to which 1 μl of T4 DNA ligase (#SDL01-R40k, Solgent, Korea) and 2 μl of 10× ligase buffer were added to make total volume of the reaction solution 20 μl, followed by ligation at 16° C. for 16 hours.

*E. coli* DH5α was transformed with the ligated plasmid, which was spread on LB plate containing ampicillin, followed by incubation in a 37° C. incubator for 16 hours. The generated colony was resuspended in LB medium containing 10 μl of ampicillin, followed by colony PCR using 4~5 μl of the medium as a template. As a result, it was confirmed that IL21R gene was successfully subcloned in the expression vector pYK602-HIS-Fc.

<1-2> Expression and Purification of IL21R-Fc 293E cells were cultured in 500 ml of DMEM supplemented with 50 ml of FBS, which was seeded in 150 mm plate with 70~80% confluency. IL21R-Fc (20 μg) was mixed with PEI (40 μg) at the ratio of 1:2, followed by reaction at room temperature for 20 minutes, which was dropped onto the cells for transfection. 16~20 hours later, the medium was replaced with 20 ml of serum free DMEM and the supernatant was obtained every 2~3 days. The obtained supernatant was centrifuged at 5000 rpm for 10 minutes. The resultant supernatant was transferred in a new bottle, which was stored at 4° C. until purification.

Total 1 l of the supernatant was obtained from 20 150 mm plates on day 3, day 5, day 7, and day 9, which proceeded to purification. The total supernatant was filtered with 0.22 μm top-filter (#PR02890 Millipore USA), which was then bound to 500 μl of protein A beads (#17-1279-03, GE healthcare, Sweden) packed in 5 ml column. Binding reaction was induced at 4° C. for overnight by using Peri-start pump (0.9 ml/minute). The column was washed with at least 100 ml of PBS. Elution was performed by using 0.1 M GLycine-HCl (#G7126, Sigma, USA) to give 6 fractions, followed by neutralization with 1 M Tris (#T-1503-5KG, Sigma, USA) (pH 9.0). Then, IL21R-Fc was quantified. 2~3 fractions showing IL21R-Fc expression were collected and concentrated by using amicon ultra (#UFC805024, Millipore, USA). Buffer was replaced with fresh PBS (#70011, Gibco, USA) about 10 times.

Figure 2:
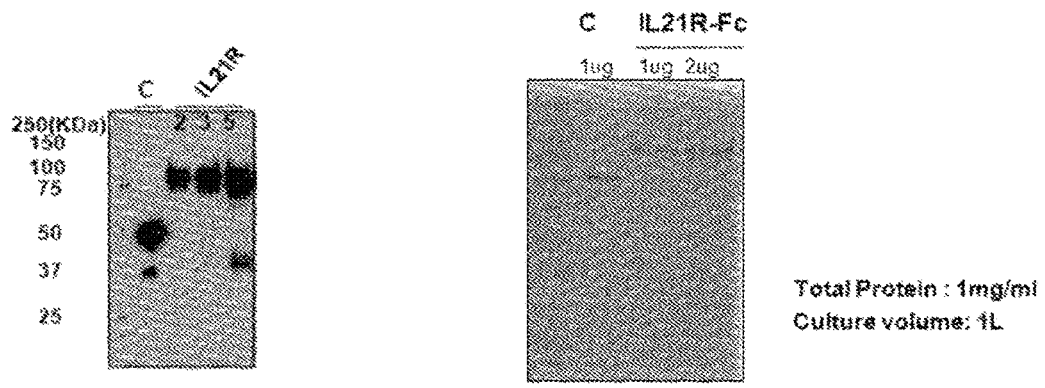
FIG. 2 is a set of photographs illustrating the result of western blot confirming the expression of IL21R-Fc cloned in the expression vector pYK602-HIS-Fc, and the result of another western blot using HIS antibody performed after purifying the expressed protein by using protein A beads.
Figure 3:
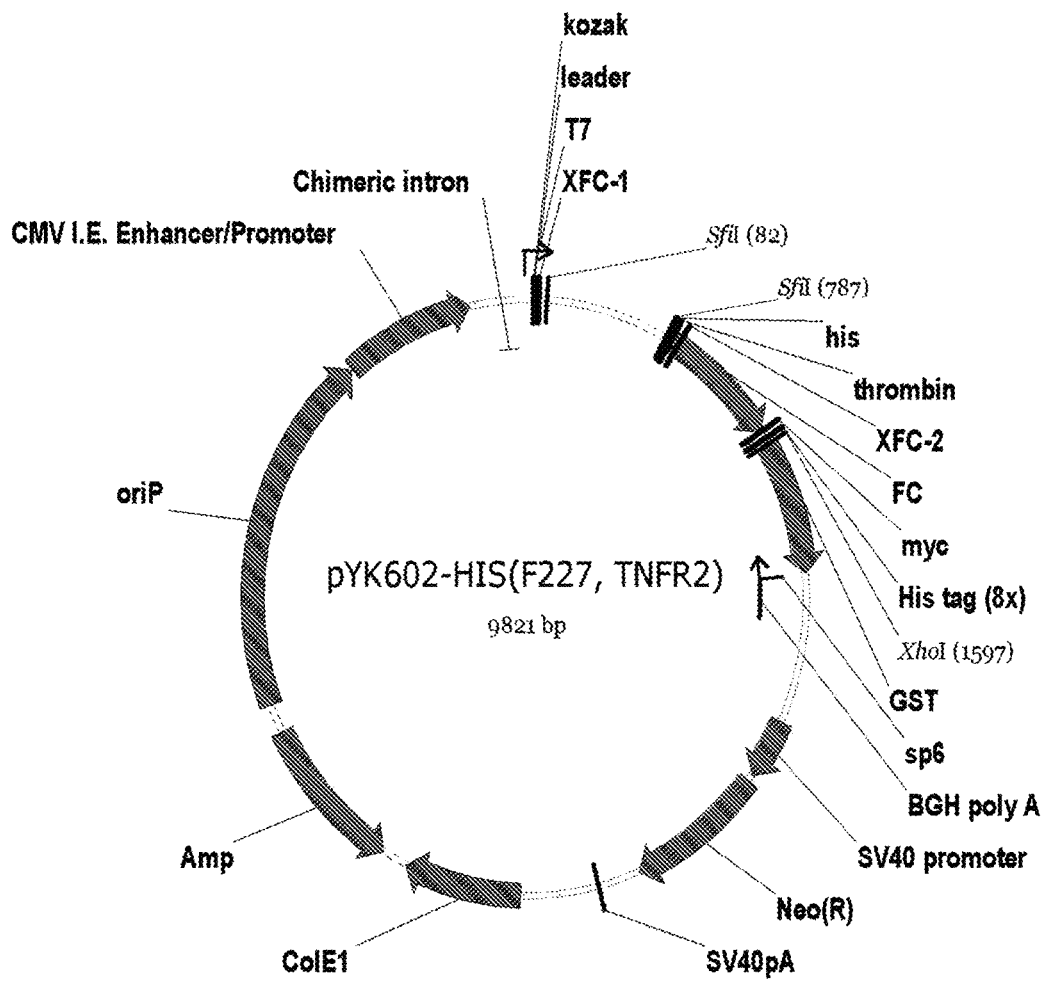
FIG. 3 is a diagram illustrating the structure of TNF-α single antagonist in which TNFR2 gene has been cloned in the expression vector pYK602-HIS-Fc.

As a result, as shown in FIG. 2, total 1.0 mg of IL21R-Fc was obtained from 1 l of supernatant (740 ng/μl).

Example 2

Construction of TNFR2-Fc

<2-1> Construction of TNFR2-Fc Expression Vector

To construct TNFR2-Fc expression vector, TNFR2 gene was amplified by PCR using DNA library mixture (mixture of kidney, placenta, pancreas, and liver; purchased from 21C Frontier Human GENE Bank (Korea Research Institute of Bioscience and Biotechnology), Clone ID: hMU013725, plate No. IRAU-86-H09, vector: pDNR-LIB) as a template with a forward primer containing Sfi I site (SEQ. ID. NO: 6: 5'-CAGGGGGCCGTGGGGGCCTTGCCCGC-CCAGGTGGCATT-3') and a reverse primer (SEQ. ID. NO: 7: 5'-TAGCGGCCGACGCGGCCAAT-TCAGCTGGGGGGCTGGGGC-3'). The PCR product was treated with Sfi I, and then subcloned into pYK602-HIS-Fc. PCR reaction mixture was prepared as follows. 100 ng of template DNA, 2.5 unit of pfu polymerase (Genotech, Korea), 10 pmole/50 μl of each primer, and distilled water were mixed to make the final volume 50 μl. PCR was performed as follows; predenaturation at 94° C. for 2 minutes, denaturation at 94° C. for 30 seconds, annealing at 55° C. for 30 seconds, polymerization at 72° C. for 1 minute, 30 cycles from denaturation to polymerization, and final extension at 72° C. for 10 minutes.

The amplified PCR product and the vector were digested with SfiI, followed by reaction at 37° C. for 4 hours. Purification was then performed by using gel purification kit. The ratio of the amplified PCR product to the vector was 3(150 μg):1(50 μg), to which 1 μl of T4 DNA ligase and 2 μl of 10× ligase buffer were added to make total volume of the reaction solution 20 μl, followed by ligation at 16° C. for 16 hours.

*E. coli* DH5α was transformed with the ligated plasmid, which was spread on LB plate containing ampicillin, followed by incubation in a 37° C. incubator for 16 hours. The generated colony was resuspended in LB medium containing 10 μl of ampicillin, followed by colony PCR using 4~5 μl of the medium as a template. As a result, it was confirmed that TNFR2 gene was successfully subcloned in the expression vector pYK602-HIS-Fc.

<2-2> Expression and Purification of TNFR2-Fc 293E cells were cultured in 500 ml of DMEM supplemented with 50 ml of FBS, which was seeded in 150 mm plate with 70~80% confluency. TNFR2-Fc (20 μg) was mixed with PEI (40 μg) at the ratio of 1:2, followed by reaction at room temperature for 20 minutes, which was dropped onto the cells for transfection. 16~20 hours later, the medium was replaced with 20 ml of serum free DMEM and the supernatant was obtained every 2~3 days. The obtained supernatant was centrifuged at 5000 rpm for 10 minutes. The resultant supernatant was transferred in a new bottle, which was stored at 4° C. until purification.

Total 1 l of the supernatant was obtained from 20 150 mm plates on day 3, day 5, day 7, and day 9, which proceeded to purification. The total supernatant was filtered with 0.22 μm top-filter, which was then bound to 500 μl of protein A beads packed in 5 ml column. Binding reaction was induced at 4° C. for overnight by using Peri-start pump (0.9 ml/minute). The column was washed with at least 100 ml of PBS. Elution was performed by using 0.1 M GLycine-HCl to give 6 fractions, followed by neutralization with 1 M Tris (pH 9.0). Then, the purified protein was quantified. 2~3 fractions showing TNFR2-Fc expression were collected and concentrated by using amicon ultra. Buffer was replaced with fresh PBS (#70011, Gibco, USA) about 10 times.

Figure 4:
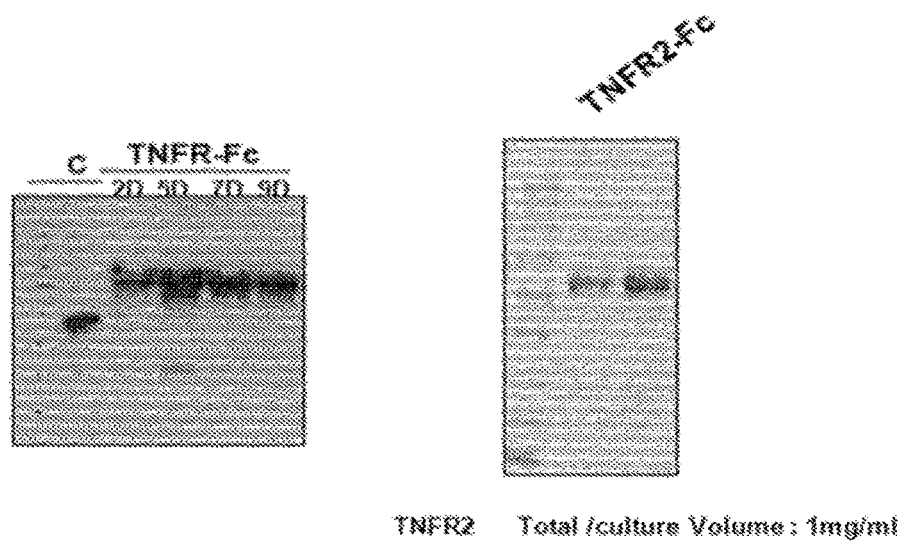
FIG. 4 is a set of photographs illustrating the result of western blot confirming the expression of TNFR2-Fc single antagonist cloned in the expression vector pYK602-HIS-Fc, and the result of another western blot using HIS antibody performed after purifying the expressed protein by using protein A beads.

As a result, as shown in FIG. 4, total 1.5 mg of TNFR2-Fc was obtained from 1 l of supernatant (1 mg/ml).

Example 3

Preparation of TNFR2-IL21R Fusion Protein

<3-1> Construction of TNFR2-IL21R Fusion Protein Expression Vector

To construct the expression vector for TNFR2-IL21R fusion protein, TNFR2 gene was amplified by PCR using DNA library mixture (mixture of kidney, placenta, pancreas, and liver) as a template with a forward primer containing Sfi I site and a reverse primer (SEQ. ID. NO: δ: 5'-tagcggc-cgacgcggccaacgtgcagactgcatccatgc-3'). IL21R gene was also amplified by PCR with a forward primer and a reverse primer under the following conditions. Two PCR products were mixed at the ratio of 1:1, which became a template at the volume of 100 ng, which proceeded to PCR with three primers, leading to subcloning of TNFR2-IL21R fusion protein into pYK602-HIS-Fc vector. PCR reaction mixture was prepared as follows. 100 ng of template DNA, 2.5 unit of pfu polymerase (Genotech, Korea), 10 pmole/50 µl of each primer, and distilled water were mixed to make the final volume 50 µl. PCR was performed as follows; predenaturation at 94° C. for 2 minutes, denaturation at 94° C. for 30 seconds, annealing at 55° C. for 30 seconds, polymerization at 72° C. for 1 minute, 30 cycles from denaturation to polymerization, and final extension at 72° C. for 10 minutes.

Each of the amplified PCR products was digested with SfiI, followed by reaction at 37° C. for 4 hours. Purification was then performed by using gel purification kit. The PCR product and vector were mixed at the ratio of 3(150 µg):1(50 µg), to which 1 µl of T4 DNA ligase and 2 µl of 10× ligase buffer were added to make total volume of the reaction solution 20 µl, followed by ligation at 16° C. for 16 hours.

E. coli DH5α was transformed with the ligated plasmid, which was spread on LB plate containing ampicillin, followed by incubation in a 37° C. incubator for 16 hours. The generated colony was resuspended in LB medium containing 10 µl of ampicillin, followed by colony PCR using 4-5 µl of the medium as a template. As a result, it was confirmed that the gene encoding TNFR2-IL21R fusion protein was successfully subcloned in the expression vector pYK602-HIS-Fc.

<3-2> Expression and Purification of TNFR2-IL21R Fusion Protein 293E cells were cultured in 500 ml of DMEM supplemented with 50 ml of FBS, which was seeded in 150 mm plate with 70~80% confluency. TNFR2-IL21R fusion protein (20 µg) was mixed with PEI (40 µg) at the ratio of 1:2, followed by reaction at room temperature for 20 minutes, which was dropped onto the cells for transfection. 16~20 hours later, the medium was replaced with 20 ml of serum free DMEM and the supernatant was obtained every 2~3 days. The obtained supernatant was centrifuged at 5000 rpm for 10 minutes. The resultant supernatant was transferred in a new bottle, which was stored at 4° C. until purification.

Total 600 ml of the supernatant was obtained from 10 150 mm plates on day 3, day 5, and day 7, which proceeded to purification. The total supernatant was filtered with 0.22 µm top-filter, which was then bound to 500 µl of protein A beads packed in 5 ml column. Binding reaction was induced at 4° C. for overnight by using Peri-start pump (0.9 ml/minute). The column was washed with at least 100 ml of PBS. Elution was performed by using 0.1 M GLycine-HCl to give 6 fractions, followed by neutralization with 1 M Tris (pH 9.0). Then, the purified protein was quantified. 2~3 fractions showing TNFR2-IL21R fusion protein expression were collected and concentrated by using amicon ultra. Buffer was replaced with fresh PBS (#70011, Gibco, USA) about 10 times.

Figure 7:
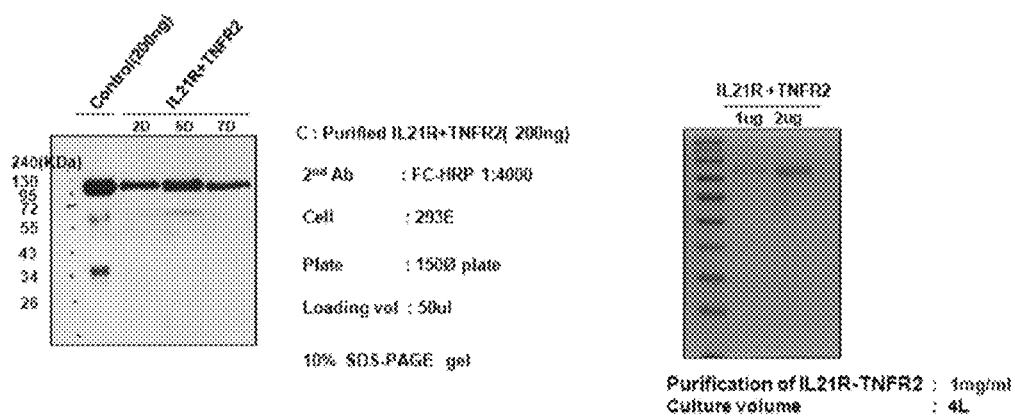
FIG. 7 is a set of photographs illustrating the result of western blot confirming the expression of TNFR2-IL21R fusion protein cloned in the expression vector pYK602-HIS-Fc.

As a result, as shown in FIG. 7, total 1 mg of TNFR2-IL21R fusion protein was obtained (380 µg/ml).

Experimental Example 1

Measurement of Binding Affinity Between TNFR2-IL21R Fusion Protein and Ligand Thereof To investigate antagonism between TNFR2-Fc, IL21R-Fc, and TNFR2-IL21R fusion protein constructed above and their ligand TNF-α, binding affinity test was performed.

Each well of the ELISA plate (#439454, Nunc, Denmark) was coated with 100 ng of TNF-α (#C001-1 MG, enzynomics, Korea) at 4° C. for overnight. Upon completion of coating, 200 µl of PBS containing 4% skim milk (#232100, Difco, France) was added to each well of the ELISA plate, followed by blocking with blocking buffer (4% skim milk in PBS) at room temperature for about 1 hour, in order to inhibit non-specific reaction. Upon completion of blocking, the blocking buffer was eliminated from the ELISA plate. Each purified fusion protein was added to 100 µl of PBS containing 1% skim milk at the concentration of 100 nM, followed by serial dilution (1/4 dilutions). Then, reaction was induced at room temperature for approximately 2 hours. Next, the plate was washed with 200 µl of PBS five times. 2 µl of anti-Human Fc-HRP (#31413, Thermo, USA), the secondary antibody, was added to 4 ml of PBS supplemented with 1% skim milk, which was distributed to each well of ELISA plate (200 µl/well), followed by reaction at room temperature for 1 hour. Upon completion of the reaction, the secondary antibody was eliminated from the ELISA plate, followed by washing with 200 µl of PBS five times. 100 µl of reaction mixture prepared by mixing 10 µl of hydrogen peroxide solution ($H_2O_2$, #H1009-100ML, Sigma, USA), 10 µl of PC buffer [5.1 g Citric acid monohydrate, 7.3 g Sodium phosphate (pH 5.0)/l], and 1 OPD tablet (#P8787-100TAB Sigma USA) was added to each well of the plate, followed by reaction at room temperature for 10 minutes at dark place. After confirming color development, the reaction was terminated by adding STOP buffer (50 µl/well). Kd value was measured at 490 nm by using ELISA reader.

As a result, as shown in FIG. 8, TNF-α ligand demonstrated low Kd value, indicating that the ligand had high binding affinity with TNFR2-IL21R fusion protein (FIG. 8).

Experimental Example 2

Inhibition of Inflammatory Cytokine by TNFR2-IL21R Fusion Protein

<2-1> Separation of Peripheral Blood Mononuclear Cells

Blood was obtained from healthy people by using heparin treated syringe, which was then diluted with PBS at the ratio of 1:1. Ficoll (Amercham Biosciences, Burkinghamshire, England) was added to the diluted blood at the ratio of 1:4, with making blood float on the top of Ficoll layer, followed by centrifugation at 2000 rpm at 20° C. for 30 minutes. Peripheral blood mononuclear cells (PBMCs) were separated from buffy coat. The separated cells were washed with PBS, and then diluted in RPMI 1640 (Gibco BRL) supplemented with 10% fetal bovine serum (Gibco, Burlingame, Calif., USA) at the density of $1 \times 10^6$ cells/ml.

<2-2> Th17 Cell Culture

The PBMCs obtained in Experimental Example <2-1> were diluted in RPMI 1640 supplemented with 10% FBS at the density of $5 \times 10^5$ cells/500 µl, which was distributed in each well of 48 well plate (Nalgen Nunc International, IL, USA). TNF-α and IL-21 antagonists TNFR2-Fc, IL21R-Fc, and TNFR2-IL21R fusion protein were treated thereto at the concentration of 10 µg/ml, followed by culture for 1 hour. 1 hour later, the cells deposited on the floor were harvested by using pipette, which were then transferred in well plate coated with anti-CD3 (BD Pharmingen, San Diego, Calif., USA) at the concentration of 0.3 µg/ml. To induce differentiation of PBMCs into Th17 cells, IL-6 (R&D Systems, Minneapolis, Minn., USA; 20 ng/ml), IL-23 (R&D Systems; 10 ng/ml), and IL-1β (R&D Systems; 5 ng/ml) were treated thereto, followed by culture in a 37° C., 5% $CO_2$ incubator. For 72 hours, the medium was not changed and additional stimulation was avoided.

<2-3> RT-PCR

Total RNA was extracted from the cells cultured for 72 hours in Experimental Example <2-2> by using RNA zol-B (Molecular Research Center, Cincinnati, Ohio, USA). 1 μl of random primer (Genotech, Daejeon, Korea) was added to the total 2 μg RNA, which stood at 70° C. for 5 minutes, followed by quick-freezing in ice. The RNA-primer mixture was mixed with 4 μl of 5×M-MULV buffer, 1 μl of 10 mM dNTP, and 0.5 μl of RNase inhibitor (Takara, Shiga, Japan), to which 9.5 μl of distilled water was added to make the total volume of the reaction solution 19 μl. Reaction was induced at 25° C. for 5 minutes, and then 1 μl of reverse transcriptase M-MULV (Takara, Shiga, Japan) was treated thereto. Reaction was induced stepwise at 25° C. for 5 minutes, at 42° C. for 60 minutes, and then at 72° C. for 10 minutes to obtain cDNA.

RT-PCR was performed by using the cDNA produced above as a template. The total volume of RT-PCR reaction mixture for each sample was 25 μl [2.5 μl of 10× reaction buffer, 2.5 μl of 0.5 mM dNTP, 0.3 μl of Taq (Takara, shinga, Japan), 2 μl of each primer (forward primer, reverse primer), 1 μl of cDNA, and 14.7 μl of distilled water]. Dual-bay thermal cycler system (MJ Research) was used for the amplification. Instead of cDNA extracted, distilled water was used for the negative control. PCR was confirmed to be free from contamination by using the negative control which did not give any PCR product. PCR for the amplification of IL-21 was performed as follows; predenaturation at 94° C. for 3 minutes, denaturation at 94° C. for 30 seconds, annealing at 56° C. for 30 seconds, polymerization at 72° C. for 30 seconds, 30 cycles from denaturation to polymerization, and final extension at 72° C. for 7 minutes. PCR for the amplification of IL-17 was performed as follows; predenaturation at 94° C. for 3 minutes, denaturation at 94° C. for 1 minute, annealing at 56° C. for 1 minute, polymerization at 72° C. for 1 minute, 30 cycles from denaturation to polymerization, and final extension at 72° C. for 7 minutes. PCR for the amplification of RORc and β-actin was performed as follows; predenaturation at 94° C. for 3 minutes, denaturation at 94° C. for 30 seconds, annealing at 60° C. for 30 seconds, polymerization at 72° C. for 30 seconds, 30 cycles or 26 cycles from denaturation to polymerization. The amplified products obtained by PCR proceeded to electrophoresis on 1.5% agarose gel containing ethidium bromide and images were obtained by using Gel-Doc 2000 (Bio-rad Laboratories, Hercules, Calif.). The amplified products were quantified by concentration measurement technique using Quantity-One program (Bio-rad). The obtained values were converted into the ratios to β-actin and then mRNA expressions among cell groups were compared. The primer sequences used herein are as follows:

```
IL-21;
                                      (SEQ. ID. NO: 9)
5'-CTT ACC TGG CAA GAC CAG TAT GA-3';

(SEQ. ID. NO: 10)
5'-GTA GAA GGC AGG GTC TTC GTA AT-3';

IL-17;
                                      (SEQ. ID. NO: 11)
5'-TGA AGT GCT GTC TGG AGC AG-3';

(SEQ. ID. NO: 12)
5'-TCC TCA GAA TCA TCC ATG TC-3';

RORc;
                                      (SEQ. ID. NO: 13)
5'-AGT CGG AAG GCA AGA TCA GA-3';

(SEQ. ID. NO: 14)
5'-CAA GAG AGG TTC TGG GCA AG-3';

β-actin;
                                      (SEQ. ID. NO: 15)
5'-GGA CTT CGA GCA AGA GAT GG-3';

(SEQ. ID. NO: 16)
5'-TGT GTT GGC GTA CAG GTC TTT G-3'.
```

The obtained values were converted into the ratios to β-actin and then mRNA expressions among cell groups were compared.

Figure 9:
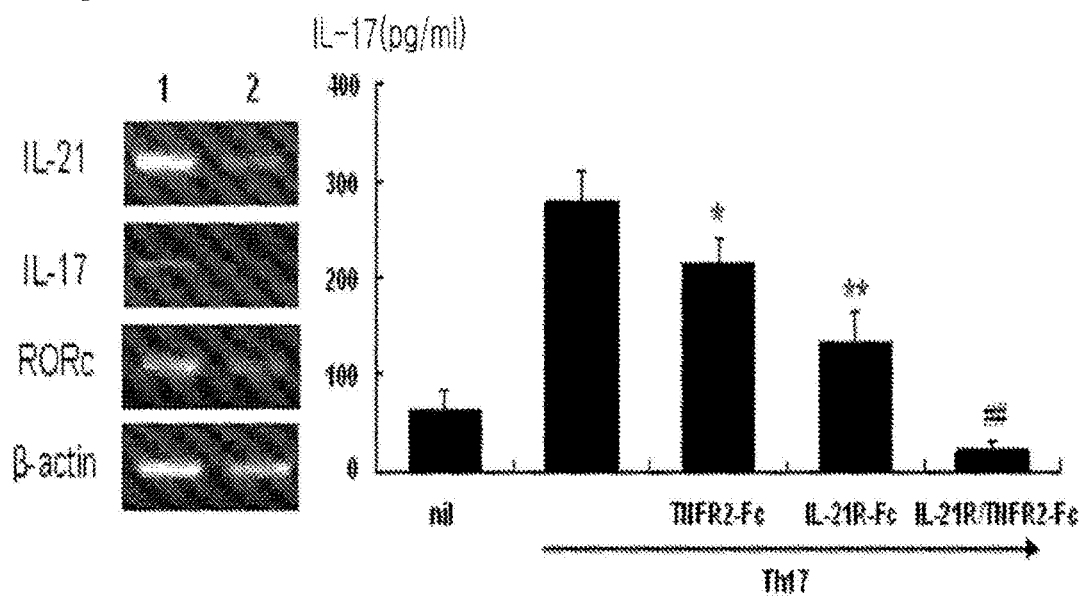
FIG. 9 is a set of photographs and a graph illustrating the result of RT-PCR confirming the expressions of IL-21, IL-17, RORc, and β-actin in Th17 cells treated with TNFR2-IL21R fusion protein, and also illustrating the quantification of inflammatory cytokine IL-17 secreted in the Th17-polarizing condition treated with TNFR2-Fc, IL21R-Fc, and TNFR2-IL21R fusion protein, respectively.

As a result, in the differentiated Th17 cells, the mRNA expression of inflammatory cytokines IL-17 and IL-21 and the specific transcription factor RORc mRNA, which has been reported to be expressed in the Th17-polarizing condition, was very high. However, when Th17 cells were treated with TNFR2-IL21R fusion protein, the expressions of IL-17, IL-21, and RORc genes were significantly suppressed (FIG. 9).

<2-4> Decrease of IL-17 Production by TNFR2-IL21R Fusion Protein

To confirm the down-regulation of IL-17 by TNFR2-IL21R fusion protein, inflammatory cytokine IL-17 in the supernatant obtained from Th17 cell culture medium treated with TNFR2-IL21R fusion protein in Example <2-3> was quantified by ELISA.

IL-10 antibody (R&D Systems) was added in 96 well plate for sandwich ELISA at the concentration of 2 μg/ml (100 μl/well), followed by reaction at room temperature for 2 hours. 200 μl of blocking buffer prepared by mixing 1% BSA with 0.05% PBST [0.05% Tween 20 in PBS] was added thereto, followed by reaction at room temperature for 2 hours. Human recombinant IL-10 (R&D Systems) to be used as a standard was serially diluted at 5,000~78.125 pg/ml. The supernatant of cell culture medium obtained in Experimental Example <3-1> to be measured along with the standard was added to each well (100 μl/well), followed by reaction at room temperature for 2 hours. Upon completion of the reaction, each well of the plate was washed with 300 μl of 0.05% PBST four times. Biotin conjugated anti-human IL-10 (R&D Systems) was diluted at the concentration of 200 ng/ml, which was distributed to each well by 100 μl/well, followed by reaction at room temperature for 2 hours. Upon completion of the reaction, the plate was washed with PBST 4 times. ExtraAvidin-Alkaline Phosphatase conjugate (Sigma, Louis, Mo., USA) was diluted at the concentration of 1:2000, which was distributed to each well by 100 μl/well, followed by reaction at room temperature for 2 hours. After washing the plate with PBST, 100 μl of phosphate disodium salt hexahydrate (PNPP)/DEA solution (1 mg/ml) was added in each well of the plate further reaction. Upon completion of the reaction, 100 μl of 0.2 N NaOH was added thereto to terminate the reaction and then $OD_{405}$ was measured.

As a result, as shown in FIG. 9, when Th17 was being differentiated, production of the inflammatory cytokine IL-17 was increased. But, when the cells were treated with the TNFR2-IL21R fusion protein of the present invention at the concentration of 10 μg/ml, IL-17 production was significantly reduced, compared with other cell groups treated with TNFR2-Fc and IL21R-Fc (FIG. 9).

Experimental Example 3

Increase of FoxP3 Expression and IL-10 Production by TNFR2-IL21R Fusion Protein <3-1> Increase of FoxP3 Expression by TNFR2-IL21R Fusion Protein To investigate whether or not TNFR2-IL21R fusion protein could increase the function of Treg, one of immune suppressive cells that keeps balance with autoantigens to protect from autoimmunity, while it suppresses Th17 cell response, the expression of FoxP3, the transcription factor generated in Treg cells, was measured by flow cytometry.

The Th17 cells differentiated by the method described in Experimental Example <2-2> were treated with 10 μg/ml of TNFR2-Fc, IL21R-Fc, and TNFR2-IL21R fusion protein, followed by culture for 1 hour. The cells were cultured for 3 days after getting same stimulation as above, to which 25 ng/ml of PMA, 250 ng/ml of Ionomycine, and Golgistop (BD Pharmingen, San Diego, Calif., USA) were treated for 5 hours. Then, the cells were harvested and treated with Peridinin chlorophyll protein (PerCP)-anti-human CD4 (Bioscience, San Diego, Calif., USA) antibody and allophycocyanin (APC)-anti-human CD25 (e-Bioscience, San Diego, Calif., USA) antibody at the concentration of 20 μl/1×10$^6$ cells, followed by reaction at 4° C. for 30 minutes at dark place. The cells were washed with FACS buffer (0.002% sodium azide, 0.2% BSA in PBS). 1 ml of permeabilization buffer was treated thereto, followed by reaction for 30 minutes. After washing the cells with permeabilization buffer, the cells were treated with Fluorescein isothiocanate-anti-human FoxP3 (e-Bioscience, San Diego, Calif., USA) at the concentration of 20 μl/1×10$^6$ cells, followed by reaction at 4° C. for 30 minutes at dark place. After washing the cells with permeabilization buffer again, the supernatant was discarded and FACS buffer was added thereto, followed by analysis with FACS Caliber (Becton Dickinson, San Diego, Calif., USA).

Figure 10:
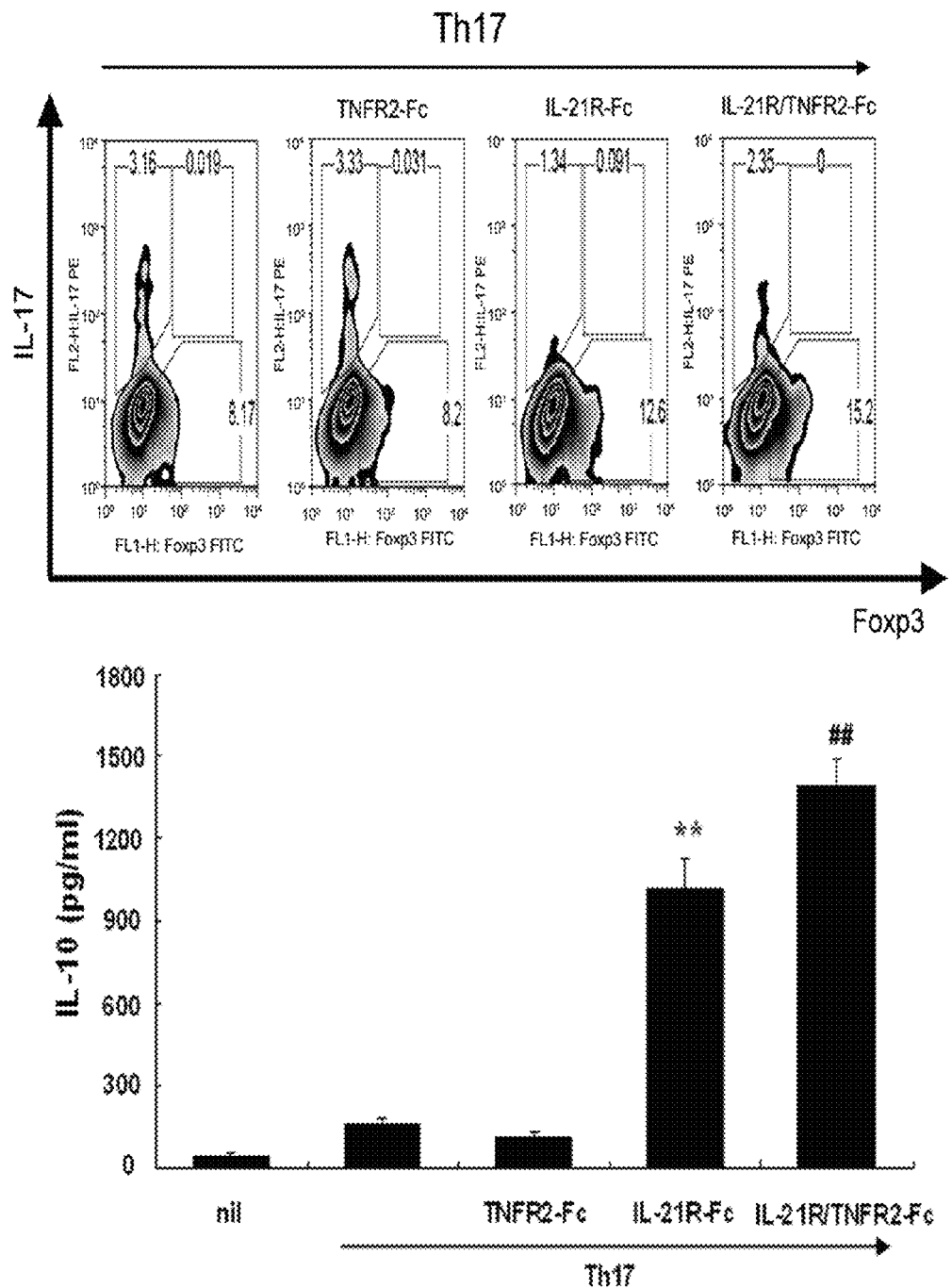
FIG. 10 is a set of graphs illustrating the expression of FoxP3 and the quantification of anti-inflammatory cytokine IL-10 in the Th17-polarizing condition treated with TNFR2-IL21R fusion protein.

As a result, as shown in FIG. 10, the expression of FoxP3, the most representative Treg transcription factor, was significantly increased when TNFR2-IL21R fusion protein was treated, compared with when TNFR2-Fc or IL21R-Fc was treated thereto (FIG. 10).

<3-2> Increase of IL-10 Production by TNFR2-IL21R Fusion Protein

To investigate whether or not TNFR2-IL21R fusion protein could increase the function of Treg, one of immune suppressive cells that keeps balance with autoantigens to protect from autoimmunity, while it suppresses Th17 cell response, the anti-inflammatory cytokine IL-10, generated in Treg cells, was quantified by ELISA.

IL-10 antibody (R&D Systems) was added in 96 well plate for sandwich ELISA at the concentration of 2 μg/ml (100 μl/well), followed by reaction at room temperature for 2 hours. 200 μl of blocking buffer prepared by mixing 1% BSA with 0.05% PBST was added thereto, followed by reaction at room temperature for 2 hours. Human recombinant IL-10 (R&D Systems) to be used as a standard was serially diluted at 5,000~78.125 pg/ml. The supernatant of cell culture medium obtained in Experimental Example <3-1> to be measured along with the standard was added to each well (100 μl/well), followed by reaction at room temperature for 2 hours. Upon completion of the reaction, each well of the plate was washed with 300 μl of 0.05% PBST four times. Biotin conjugated anti-human IL-10 (R&D Systems) was diluted at the concentration of 200 ng/ml, which was distributed to each well by 100 μl/well, followed by reaction at room temperature for 2 hours. Upon completion of the reaction, the plate was washed with PBST 4 times. ExtraAvidin-Alkaline Phosphatase conjugate (Sigma, Louis, Mo., USA) was diluted at the concentration of 1:2000, which was distributed to each well by 100 μl/well, followed by reaction at room temperature for 2 hours. After washing the plate with PBST, 100 μl of phosphate disodium salt hexahydrate (PNPP)/DEA solution (1 mg/ml) was added in each well of the plate for further reaction. Upon completion of the reaction, 100 μl of 0.2 N NaOH was added thereto to terminate the reaction and then OD$_{405}$ was measured.

As a result, as shown in FIG. 10, IL-10 production was significantly increased when TNFR2-IL21R fusion protein was treated into Th17-polarizing condition, compared with when TNFR2-Fc or IL21R-Fc was treated (FIG. 10).

Experimental Example 4

Decrease of Osteoclast Differentiation by TNFR2-IL21R Fusion Protein

<4-1> Osteoclast Culture

Blood was obtained from healthy people by using heparin treated syringe, which was then diluted with PBS at the ratio of 1:1. Ficoll was added to the diluted blood at the ratio of 1:4, with making blood float on the top of Ficoll layer, followed by centrifugation at 2000 rpm at 20° C. for 30 minutes. Peripheral blood mononuclear cells were separated from buffy coat. The separated cells were washed with PBS, and then diluted in αMEM (Invitrogen, Burlingame, Calif., USA) supplemented with 10% fetal bovine serum. The cells were distributed in 24 well plate at the density of 5×10$^5$ cells/500 μl, followed by culture in a 37° C., 5% CO$_2$ incubator for 2 hours. 2 hours later, the cells not attached on the bottom were eliminated. After washing with PBS, 500 μl of 10% αMEM was added thereto. The cells were stimulated with 100 ng/ml of recombinant human macrophage/monocyte colony-forming factor (M-CSF, R&D Systems, Minneapolis, Minn., USA), followed by culture for 3 days. 3 days later, the cells were washed with PBS and the culture solution was replaced with fresh 10% αMEM. The cells were stimulated again with 25 ng/ml of rhM-CSF and 30 ng/ml of receptor activator of nuclear factor kappa B ligand (RANKL, Peprotech, London, UK). Then, TNFR2-Fc, IL21R-Fc, and TNFR2-IL21R fusion protein were treated to the cells at the concentration of 10 μg/ml respectively, followed by further culture. Culture medium was replaced every 3 days and treated again with the above stimulation condition. Cell differentiation was observed to determine stimulation frequency.

<4-2> Osteoclast Staining

The differentiated cells were treated with the TNF-α and IL-21 antagonists TNFR2-Fc, IL21R-Fc, and TNFR2-IL21R fusion protein, to induce osteoclast differentiation by the same manner as described above. The differentiated osteoclasts were fixed with 10% formalin. After washing the cells with PBS three times, the differentiated osteoclasts were examined by using Tartrate-resistant acid phosphatase (TRAP) staining Kit (Sigma, Louis, Mo., USA). 45 ml of pre-heated sterilized distilled water (37° C.) was mixed with 500 μl of fast Garmet GBC Basr solution and 500 μl of sodium nitrite solution in the kit. 500 μl of Naphthol AS-BI Phosphate solution, 2 ml of acetate solution, and 1 ml of Tartrate solution were added to the mixed solution stepwise. After well mixing, the mixture was loaded to the fixed cells by 200 μl, followed by staining at 37° C. for 30 minutes. Reaction time was regulated by observing staining grades. TRAP-positive (reddish purple) multinuclear cells having at least 3 nuclei were regarded as osteoclasts, which was identified under optical microscope. Experiment was performed at least three times with 4 grouped wells and the results were presented by mean±standard deviation.

Figure 11:
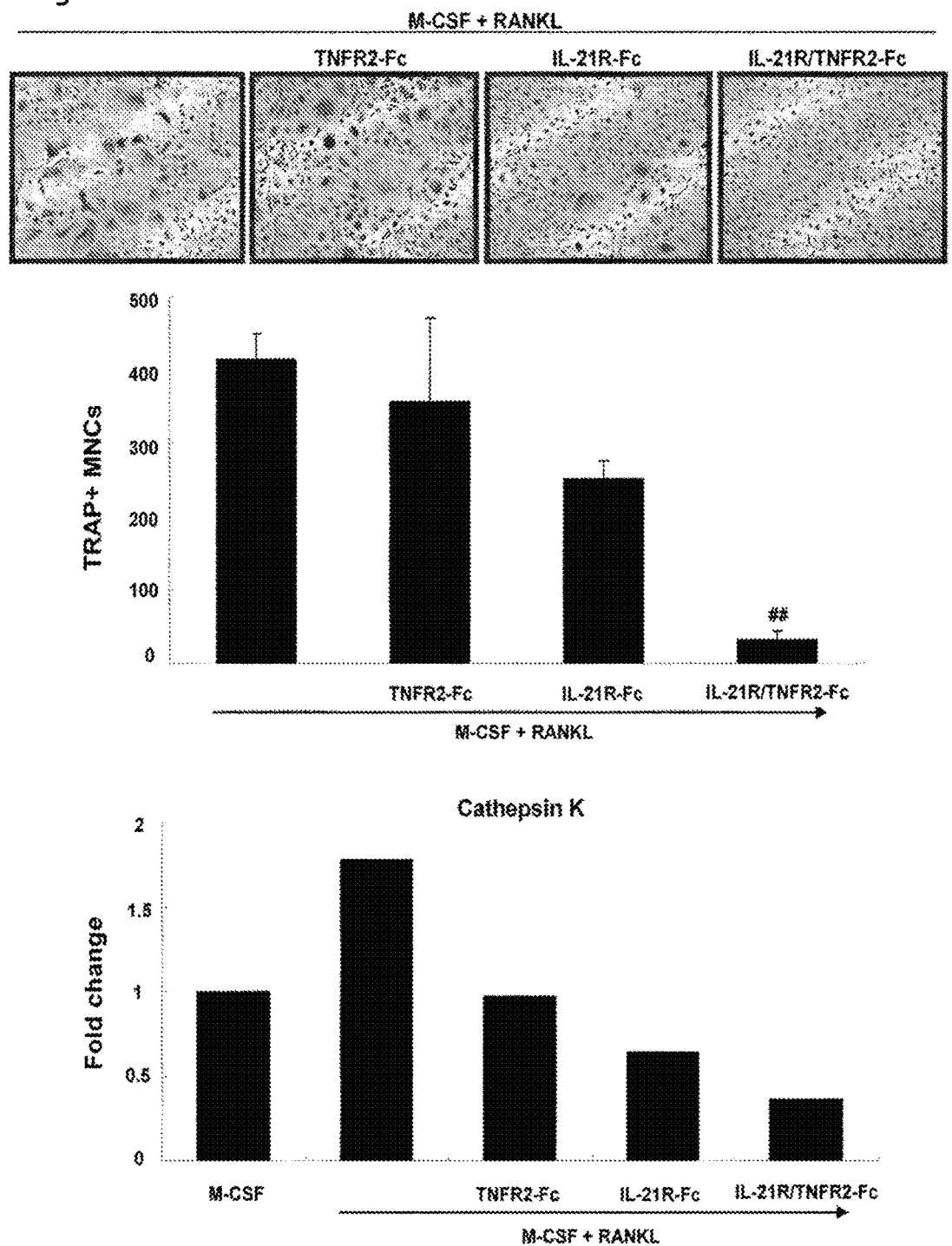
FIG. 11 is a set of photographs and graphs illustrating the inhibitory effect of TNFR2-IL21R fusion protein on osteoclast differentiation.

As a result, as shown in FIG. 11, osteoclast differentiation was actively undergoing by the stimulation of M-CSF and RANKL. Such differentiation was, however, effectively inhibited by the treatment of TNFR2-IL21R fusion protein, compared with when TNFR2-Fc and IL21R-Fc were treated (FIG. 11).

<4-3> Expression of Cathepsin K

RNA was extracted from the differentiated cells treated with TNFR2-Fc, IL21R-Fc, and TNFR2-IL21R fusion protein, from which cDNA was synthesized by RT-PCR by the same manner as described in Experimental Example <2-3> to measure the expression of Cathepsin K.

As a result, as shown in FIG. 11, Cathepsin K expression induced by the stimulation of M-CSF and RANKL was more significantly inhibited by the treatment of TNFR2-IL21R fusion protein, compared with when TNFR2-Fc and IL21R-Fc were treated (FIG. 11).

Experimental Example 5

Treatment Effect of TNFR2-IL21R Fusion Protein on Arthritis in CIA Mouse Model

To investigate the treatment effect of the TNFR2-IL21R fusion protein of the present invention on arthritis, CIA (collagen induced arthritis) mouse model was treated with TNFR2-IL21R fusion protein. Then, treatment effect was investigated.

Particularly, to induce CIA, DBA/1J mice (OrientBio, Korea) at 6 weeks were injected at the tail with 100 μg of type II collagen (CII) mixed with same amount of complete Freund's adjuvant (CFA), leading to the primary immunization. Each experimental group had 6 mice. From a week (7 days) after the immunization, the mice were administered with 50 μg of IL21R/TNFR2-Fc (TNFR2-IL21R fusion protein) and 100 μg of Enbrel by intraperitoneal injection (I.P.) three times per week for three weeks (9 times total). Three investigators observed joint inflammation three times a week starting from the primary immunization. Evaluation was performed by mean arthritic index as follows; points are given grade by grade; points given are all added up and divided by 4 to give mean value; means obtained from three different investigators for each mouse are added, from which average was obtained. One leg was given 25%, based on which the number of the swollen legs was calculated, resulting in incidence:

0 point: none of edema or swelling;

1 point: light edema and redness limited in food or ankle joint;

2 points: light edema and redness over metatarsal from ankle joint;

3 points: severe edema and redness over metatarsal from ankle joint; and 4 points: edema and redness all over the leg from ankle.

Figure 12:
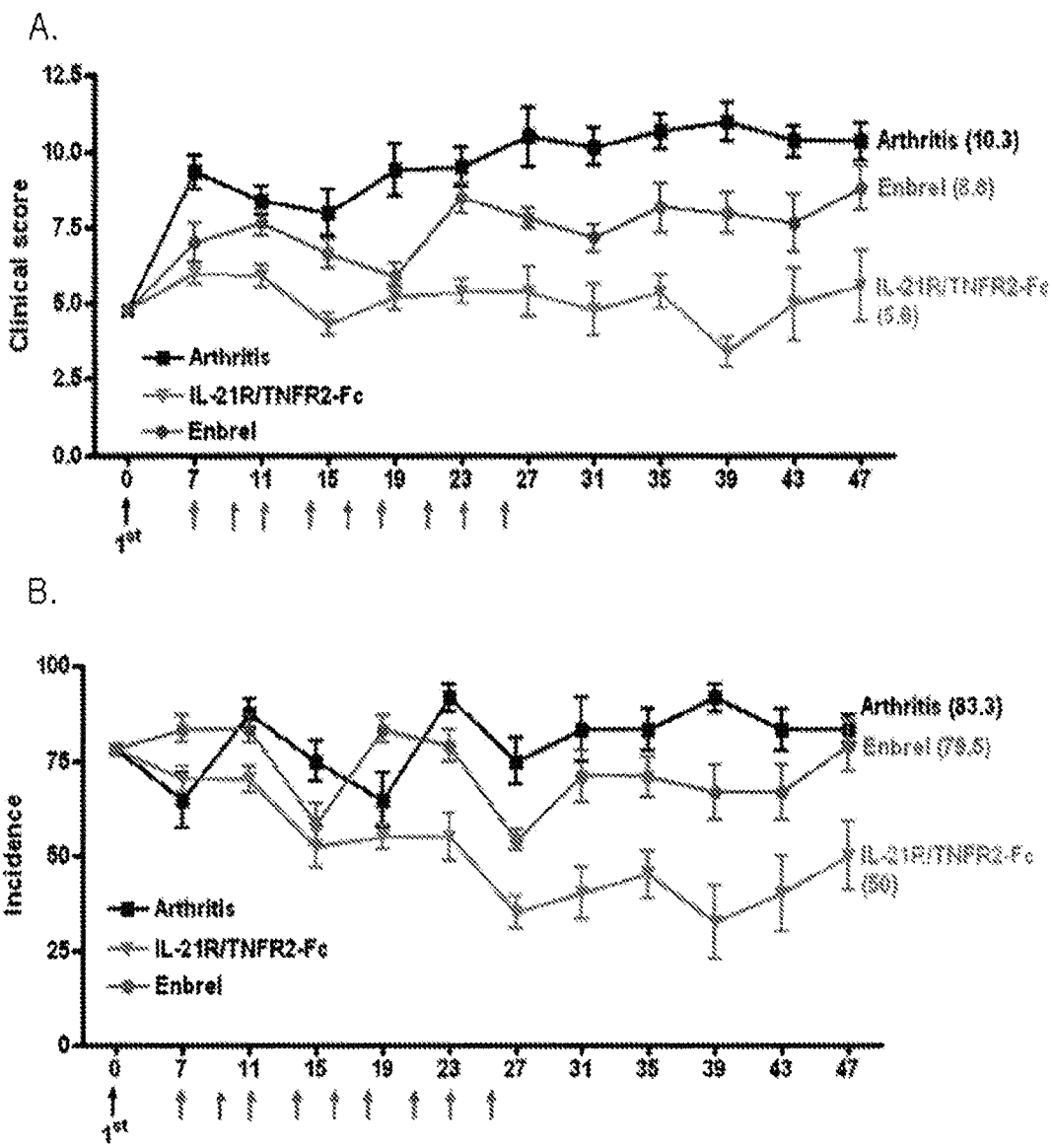
FIG. 12 is a set of graphs illustrating the treatment effect of TNFR2-IL21R fusion protein on arthritis in CIA mouse model.

As a result, as shown in FIG. 12, it was confirmed by observing clinical score and incidence that excellent arthritis treatment effect was demonstrated in the CIA mouse model group treated with the TNFR2-IL21R fusion protein of the present invention. Such treatment effect was greater than that observed in the positive control group treated with Enbrel, the conventional arthritis treatment agent (FIG. 12).

Experimental Example 6

Confirmation of Alleviation Effect of RNFR2-IL21R Fusion Protein on Arthritis in CIA Mouse Model by Immunohistochemical Staining Joints were extracted from the experimental CIA mouse model groups treated with TNFR2-IL21R fusion protein and Enbrel of Experimental Example 5. Immunohistochemical staining was performed to investigate infiltration and inflammation in joint and cartilage destruction.

Particularly, to perform immunohistochemical staining, joints were taken from CIA mice respectively treated with TNFR2-IL21R fusion protein and Enbrel. Then, the joints were fixed in 10% neutral buffered formalin and bones were decalcified with EDTA. The joint tissues were embedded in paraffin. The paraffin embedded joint tissues were made into 7 μm thick sections, which were placed on slide. Before staining, deparaffination was performed by using xylene, during which dehydration was also performed with ethanol (high conc.→low conc.). Then haematoxylin and eosin staining was performed. Cartilage destruction and inflammation were measured by using Safranin O and Toluidine blue method that is able to detect proteoglycans included in cartilage.

As a result, as shown in FIG. 13, cellular infiltration was remarkably reduced when CIA mouse model was treated with TNFR2-IL21R fusion protein, compared with when nothing was treated. It was also observed by using Safranin O and Toluidine blue method that inflammation and destruction of cartilage were alleviated when TNFR2-IL21R fusion protein was treated (FIG. 13).

Experimental Example 7

Confirmation of Alleviation Effect of TNFR2-IL21R Fusion Protein on Inflammation in CIA Mouse Model by Immunohistochemical Staining Joints were extracted from the experimental CIA mouse model groups treated with TNFR2-IL21R fusion protein and Enbrel of Experimental Example 5. Immunohistochemical staining was performed to investigate the expressions of inflammatory factors.

Particularly, joints were taken from CIA mice respectively treated with TNFR2-IL21R fusion protein and Enbrel. Then, the joints were fixed in 10% neutral buffered formalin and bones were decalcified with EDTA. The joint tissues were embedded in paraffin. The paraffin embedded joint tissues were made into 7 μm thick sections, which were placed on slide. Before staining, deparaffination was performed by using xylene, during which dehydration was also performed with ethanol (high conc.→low conc.). The inflammatory cytokines IL-17, TNF-α, IL-1β, and IL-6, and Receptor activator of nuclear factor-κB (RANK), and Vascular endothelial growth factor (VEGF) were stained by the method of immunohistochemical staining, followed by observation under optical microscope.

As a result, as shown in FIG. 14, the expressions of the inflammatory cytokines IL-17, TNF-α, IL-1β, and IL-6 were all decreased in the group treated with the TNFR2-IL21R fusion protein of the present invention, compared with the other CIA mouse model groups not treated with the fusion protein. Besides, the expressions of VEGF, the important factor for angiogenesis, and RANK that is the factor showing osteoclast differentiation were hardly observed. Such expression patterns of inflammatory cytokines, VEGF, and RANK in the group treated with TNFR2-IL21R fusion protein were consistent with the aspect of the group treated with Enbrel, suggesting that the TNFR2-IL21R fusion protein of the present invention can also be effectively used for the treatment of arthritis (FIG. 14).

Experimental Example 8

CII Specific IgG2a Production in CIA Mouse Model

The CIA mouse model used in Experimental Example 5 was immunized by one time injection of type II Collagen (CII). Then, the TNFR2-IL21R fusion protein of the present invention was administered to the animal three times a week for three weeks (9 times total). Blood CII was measured during the administration period.

100 μg of CII mixed with the same amount of complete Freund's adjuvant (CFA) was injected into the tails of DAB mice. One week later, the TNFR2-IL21R fusion protein of the present invention was administered to the mice 9 times in total for three weeks. Blood was taken from the eyes of the mice before the administration of TNFR2-IL21R fusion protein (0), after the first administration, after the $6^{th}$ administration, and within 6~12 hours after the last administration, to obtain serum. To measure the amount of CII-specific IgG2a, CII antibody was diluted at the ratio of 1:1,000, with which 96 well plate was coated, followed by reaction for 2 hours. After eliminating the coating buffer, 200 μl of blocking buffer was added to each well, followed by reaction at room temperature for 1 hour. Then, serum of experimental group or control group was diluted, which was added thereto (50 μl/well), followed by reaction at room temperature for 1 hour. After washing the plate with IgG washing buffer 5 times, anti-mouse IgG HRP (1:75,000) was added thereto (50 μl/well), followed by reaction at room temperature for 1 hour. Upon completion of the reaction, the plate was washed with IgG washing buffer 5 times, followed by reaction with TMB substrate solution. Color development was stopped by using 1N $H_2SO_4$, and then $OD_{450}$ was measured with ELISA reader.

As a result, as shown in FIG. 15, the amount of CII-specific IgG2a was not changed over the time in CIA mouse model group not treated with any Fc fusion protein. However, in the group treated with TNFR2-IL21R fusion protein, the amount of CII-specific IgG2a was decreased over the administration times. In addition, in the group treated with Enbrel, OD value seemed to be slightly increased after the first administration, but began to decrease after the additional Enbrel administration (FIG. 15).

Experimental Example 9

Measurement of Th17 and Treg Cells Expressions in Spleen of CIA Mouse Model

To investigate the effect of the TNFR2-IL21R fusion protein of the present invention on the expressions of Th17 and Treg cells in CIA mouse model, spleen tissues were extracted from the mice used in Experimental Example 5. Then, Th17 (CD4+IL-17+) and Treg (CD4+CD25+Foxp3+) cells were observed by confocal microscopy of immunostaining.

Particularly, spleen was extracted from the CIA mouse model of Experimental Example 5, which was embedded with OCT compound. The tissues were quick-frozen by using liquid nitrogen, which were sliced into 7 μm sections by using cryotome and then placed on slide. The section placed on the slide was fixed with acetone and non-specific reaction was blocked by using 10% normal goat serum for 30 minutes. Staining of the Treg markers, CD4, CD25, and Foxp3, was performed by using PE-labeled anti-CD4 antibody, Allophycocyanin-labeled anti-CD25 antibody (Biolegend), and FITC-labeled anti-Foxp3 Ab antibody. Staining of the Th17 markers, CD4, and IL-17, was performed by using biotinylated anti-CD4 antibody (BD Biosciences), and PE-labeled anti-IL-17 antibody. The said antibodies were diluted in PBS (pH 7.5) at the ratio of 1:100, followed by reaction with the tissues placed on the slide at 4° C. for overnight. On the next day, the tissues reacted with biotinylated anti-CD4 antibody were additionally reacted with streptavidin cy-3 at room temperature for 2 hours. After washing the slide with PBS three times, the stained tissues were observed under confocal microscope (LSM 510 Meta. Zeiss, Gottingen, Germany).

As a result, as shown in FIG. 16, in the spleen tissues obtained from the CIA mouse model treated with the TNFR2-IL21R fusion protein of the present invention, the number of Foxp3+ cells was increased, compared with the CIA mouse model treated with nothing. In the meantime, the expression of Th17 (CD4+IL-17+) was reduced in the group treated with TNFR2-IL21R fusion protein or Enbrel, compared with the CIA mouse model treated with nothing (FIG. 16).

The Manufacturing Examples of the composition of the present invention are described hereinafter.

Manufacturing Example 1

Preparation of Pharmaceutical Formulations

<1-1> Preparation of Powders

| | |
|---|---|
| TNFR2-IL21R fusion protein | 2 g |
| Lactose | 1 g |

Powders were prepared by mixing all the above components, which were filled in airtight packs according to the conventional method for preparing powders.

<1-2> Preparation of Tablets

| | |
|---|---|
| TNFR2-IL21R fusion protein | 100 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| TNFR2-IL21R fusion protein | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Pills

| | |
|---|---|
| TNFR2-IL21R fusion protein | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| | |
|---|---|
| TNFR2-IL21R fusion protein | 150 mg |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

INDUSTRIAL APPLICABILITY

As explained hereinbefore, the TNFR2-IL21R fusion protein of the present invention inhibits the secretion of IL-17, the inflammatory cytokine, which is one of major causes of rheumatoid arthritis, one of most representative autoimmune diseases, in Th17 cells, increases the expression of FoxP3 in Treg cells, increases the secretion of IL-10, the anti-inflammatory cytokine, suppresses the expression of cathespin K, and inhibits the differentiation of osteoclasts. Therefore, it is suggested that the TNFR2-IL21R fusion protein of the present invention demonstrates better effect than TNFR2-Fc or IL21R-Fc. When the TNFR2-IL21R fusion protein of the present invention was administered to CIA (collagen induced Arthritis) animal model, it inhibited infiltration and inflammation in joint, reduced the destruction of cartilage, increased the expression of Tregs, the immune suppressive cells, and demonstrated treatment effect on autoimmune rheumatoid arthritis. Therefore, the TNFR2-IL21R fusion protein of the present invention can be effectively used as an active ingredient for the composition for the prevention and treatment of autoimmune disease.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

SEQUENCE LISTING

```
<160> NUMBER OF SEQ ID NOS: 16

<210> SEQ ID NO 1
<211> LENGTH: 403
<212> TYPE: PRT
<213> ORGANISM: Artificial Sequence
<220> FEATURE:
<223> OTHER INFORMATION: TNF receptor alpha 2 and IL21 receptor fusion
      protein

<400> SEQUENCE: 1

Gln Gly Ala Val Gly Ala Pro Asp Leu Val Cys Tyr Thr Asp Tyr Leu
1               5                   10                  15

Gln Thr Val Ile Cys Ile Leu Glu Met Trp Asn Leu His Pro Ser Thr
            20                  25                  30

Leu Thr Leu Thr Trp Gln Asp Gln Tyr Glu Glu Leu Lys Asp Glu Ala
        35                  40                  45

Thr Ser Cys Ser Leu His Arg Ser Ala His Asn Ala Thr His Ala Thr
    50                  55                  60

Tyr Thr Cys His Met Asp Val Phe His Phe Met Ala Asp Asp Ile Phe
65                  70                  75                  80

Ser Val Asn Ile Thr Asp Gln Ser Gly Asn Tyr Ser Gln Glu Cys Gly
                85                  90                  95

Ser Phe Leu Leu Ala Glu Ser Ile Lys Pro Ala Pro Pro Phe Asn Val
            100                 105                 110

Thr Val Thr Phe Ser Gly Gln Tyr Asn Ile Ser Trp Arg Ser Asp Tyr
        115                 120                 125

Glu Asp Pro Ala Phe Tyr Met Leu Lys Gly Lys Leu Gln Tyr Glu Leu
    130                 135                 140

Gln Tyr Arg Asn Arg Gly Asp Pro Trp Ala Val Ser Pro Arg Arg Lys
145                 150                 155                 160

Leu Ile Ser Val Asp Ser Arg Ser Val Ser Leu Leu Pro Leu Glu Phe
                165                 170                 175

Arg Lys Asp Ser Ser Tyr Glu Leu Gln Val Arg Ala Gly Pro Met Pro
            180                 185                 190

Gly Ser Ser Tyr Gln Gly Thr Trp Ser Glu Trp Ser Asp Pro Val Ile
```

```
                195                 200                 205
    Phe Gln Thr Gln Ser Glu Glu Leu Lys Glu Leu Pro Ala Gln Val Ala
    210                 215                 220

Phe Thr Pro Tyr Ala Pro Glu Pro Gly Ser Thr Cys Arg Leu Arg Glu
225                 230                 235                 240

Tyr Tyr Asp Gln Thr Ala Gln Met Cys Cys Ser Lys Cys Ser Pro Gly
                    245                 250                 255

Gln His Ala Lys Val Phe Cys Thr Lys Thr Ser Asp Thr Val Cys Asp
                260                 265                 270

Ser Cys Glu Asp Ser Thr Tyr Thr Gln Leu Trp Asn Trp Val Pro Glu
                275                 280                 285

Cys Leu Ser Cys Gly Ser Arg Cys Ser Ser Asp Gln Val Glu Thr Gln
    290                 295                 300

Ala Cys Thr Arg Glu Gln Asn Arg Ile Cys Thr Cys Arg Pro Gly Trp
    305                 310                 315                 320

Tyr Cys Ala Leu Ser Lys Gln Glu Gly Cys Arg Leu Cys Ala Pro Leu
                    325                 330                 335

Arg Lys Cys Arg Pro Gly Phe Gly Val Ala Arg Pro Gly Thr Glu Thr
                340                 345                 350

Ser Asp Val Val Cys Lys Pro Cys Ala Pro Gly Thr Phe Ser Asn Thr
                355                 360                 365

Thr Ser Ser Thr Asp Ile Cys Arg Pro His Gln Ile Cys Asn Val Val
    370                 375                 380

Ala Ile Pro Gly Asn Ala Ser Met Asp Ala Val Cys Thr Leu Ala Ala
    385                 390                 395                 400

Ser Ala Ala

<210> SEQ ID NO 2
<211> LENGTH: 230
<212> TYPE: PRT
<213> ORGANISM: Homo sapiens

<400> SEQUENCE: 2

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
```

```
              165                 170                 175
Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu
225                 230

<210> SEQ ID NO 3
<211> LENGTH: 213
<212> TYPE: PRT
<213> ORGANISM: Homo sapiens

<400> SEQUENCE: 3

Pro Asp Leu Val Cys Tyr Thr Asp Tyr Leu Gln Thr Val Ile Cys Ile
1               5                   10                  15

Leu Glu Met Trp Asn Leu His Pro Ser Thr Leu Thr Leu Thr Trp Gln
            20                  25                  30

Asp Gln Tyr Glu Glu Leu Lys Asp Glu Ala Thr Ser Cys Ser Leu His
        35                  40                  45

Arg Ser Ala His Asn Ala Thr His Ala Thr Tyr Thr Cys His Met Asp
    50                  55                  60

Val Phe His Phe Met Ala Asp Asp Ile Phe Ser Val Asn Ile Thr Asp
65                  70                  75                  80

Gln Ser Gly Asn Tyr Ser Gln Glu Cys Gly Ser Phe Leu Leu Ala Glu
                85                  90                  95

Ser Ile Lys Pro Ala Pro Pro Phe Asn Val Thr Val Thr Phe Ser Gly
            100                 105                 110

Gln Tyr Asn Ile Ser Trp Arg Ser Asp Tyr Glu Asp Pro Ala Phe Tyr
        115                 120                 125

Met Leu Lys Gly Lys Leu Gln Tyr Glu Leu Gln Tyr Arg Asn Arg Gly
    130                 135                 140

Asp Pro Trp Ala Val Ser Pro Arg Arg Lys Leu Ile Ser Val Asp Ser
145                 150                 155                 160

Arg Ser Val Ser Leu Leu Pro Leu Glu Phe Arg Lys Asp Ser Ser Tyr
                165                 170                 175

Glu Leu Gln Val Arg Ala Gly Pro Met Pro Gly Ser Ser Tyr Gln Gly
            180                 185                 190

Thr Trp Ser Glu Trp Ser Asp Pro Val Ile Phe Gln Thr Gln Ser Glu
        195                 200                 205

Glu Leu Lys Glu Leu
    210

<210> SEQ ID NO 4
<211> LENGTH: 37
<212> TYPE: DNA
<213> ORGANISM: Artificial Sequence
<220> FEATURE:
<223> OTHER INFORMATION: IL21R forward primer

<400> SEQUENCE: 4 aggggggccgt gggggccccc gacctcgtct gctacac                          37

<210> SEQ ID NO 5
<211> LENGTH: 39
```

<212> TYPE: DNA
<213> ORGANISM: Artificial Sequence
<220> FEATURE:
<223> OTHER INFORMATION: IL21R reward primer

<400> SEQUENCE: 5
tagcggccga cgcggccaat tcctttaact cctctgact                    39

<210> SEQ ID NO 6
<211> LENGTH: 38
<212> TYPE: DNA
<213> ORGANISM: Artificial Sequence
<220> FEATURE:
<223> OTHER INFORMATION: TNFR2 forward primer

<400> SEQUENCE: 6 caggggccg tggggccctt gcccgcccag gtggcatt                      38

<210> SEQ ID NO 7
<211> LENGTH: 39
<212> TYPE: DNA
<213> ORGANISM: Artificial Sequence
<220> FEATURE:
<223> OTHER INFORMATION: TNFR2 reward primer

<400> SEQUENCE: 7
tagcggccga cgcggccaat tcagctgggg ggctggggc                    39

<210> SEQ ID NO 8
<211> LENGTH: 39
<212> TYPE: DNA
<213> ORGANISM: Artificial Sequence
<220> FEATURE:
<223> OTHER INFORMATION: Forward primer for TNFR2-IL21R fusion protein

<400> SEQUENCE: 8
tagcggccga cgcggccaac gtgcagactg catccatgc                    39

<210> SEQ ID NO 9
<211> LENGTH: 23
<212> TYPE: DNA
<213> ORGANISM: Artificial Sequence
<220> FEATURE:
<223> OTHER INFORMATION: IL-21 forward primer for PCR

<400> SEQUENCE: 9
cttacctggc aagaccagta tga                                     23

<210> SEQ ID NO 10
<211> LENGTH: 23
<212> TYPE: DNA
<213> ORGANISM: Artificial Sequence
<220> FEATURE:
<223> OTHER INFORMATION: IL-21 reward primer for PCR

<400> SEQUENCE: 10
gtagaaggca gggtcttcgt aat                                     23

<210> SEQ ID NO 11
<211> LENGTH: 20
<212> TYPE: DNA
<213> ORGANISM: Artificial Sequence
<220> FEATURE:
<223> OTHER INFORMATION: IL-17 forward primer

<400> SEQUENCE: 11

```
<210> SEQ ID NO 12
<211> LENGTH: 20
<212> TYPE: DNA
<213> ORGANISM: Artificial Sequence
<220> FEATURE:
<223> OTHER INFORMATION: IL-17 reward primer

<400> SEQUENCE: 12
tcctcagaat catccatgtc                                              20

<210> SEQ ID NO 13
<211> LENGTH: 20
<212> TYPE: DNA
<213> ORGANISM: Artificial Sequence
<220> FEATURE:
<223> OTHER INFORMATION: RORc forward primer

<400> SEQUENCE: 13
agtcggaagg caagatcaga                                              20

<210> SEQ ID NO 14
<211> LENGTH: 20
<212> TYPE: DNA
<213> ORGANISM: Artificial Sequence
<220> FEATURE:
<223> OTHER INFORMATION: RORc reward primer

<400> SEQUENCE: 14
caagagaggt tctgggcaag                                              20

<210> SEQ ID NO 15
<211> LENGTH: 20
<212> TYPE: DNA
<213> ORGANISM: Artificial Sequence
<220> FEATURE:
<223> OTHER INFORMATION: beta actin forward primer

<400> SEQUENCE: 15
ggacttcgag caagagatgg                                              20

<210> SEQ ID NO 16
<211> LENGTH: 22
<212> TYPE: DNA
<213> ORGANISM: Artificial Sequence
<220> FEATURE:
<223> OTHER INFORMATION: beta actin reward primer

<400> SEQUENCE: 16
tgtgttggcg tacaggtctt tg                                           22
```

(preceding line: `tgaagtgctg tctggagcag     20`)

What is claimed is:

1. A method for the treatment of autoimmune disease comprising administering a pharmaceutically effective dose of a fusion protein to a subject with autoimmune disease, wherein the fusion protein consists of the extracellular domain of TNFR2 (tumor necrosis factor receptor type 2) protein fused to the extracellular domain of IL21R (interleukin-21 receptor) protein, wherein the fusion protein consists of the amino acid sequence 7-397 of SEQ ID NO: 1.

2. The method according to claim 1, wherein the extracellular domain of TNFR2 protein consists of the amino acid sequence 1-179 of SEQ ID NO: 2.

3. The method according to claim 1, wherein the extracellular domain of IL21R protein consists of the amino acid sequence 1-212 of SEQ ID NO: 3.

4. The method according to claim 1, wherein the autoimmune disease is selected from the group consisting of pernicious anemia, type 1 diabetes, autoimmune arthritis, lupus, multiple sclerosis, reactive arthritis, and dermatomyositis.

* * * * *